(12) United States Patent
Bradley

(10) Patent No.: US 7,006,869 B2
(45) Date of Patent: Feb. 28, 2006

(54) METHOD AND DEVICE FOR ENHANCED CAPTURE TRACKING BY DISCRIMINATION OF FUSION BEATS

(75) Inventor: Kerry Bradley, Glendale, CA (US)

(73) Assignee: Pacesetter, Inc., Sylmar, CA (US)

(*) Notice: Subject to any disclaimer, the term of this patent is extended or adjusted under 35 U.S.C. 154(b) by 299 days.

(21) Appl. No.: 09/952,458

(22) Filed: Sep. 10, 2001

(65) Prior Publication Data

US 2003/0050671 A1 Mar. 13, 2003

(51) Int. Cl.
*A61N 1/37* (2006.01)

(52) U.S. Cl. ............................................. 607/28

(58) Field of Classification Search ............... 607/4, 607/9, 27–28
See application file for complete search history.

(56) References Cited

U.S. PATENT DOCUMENTS

| | | | |
|---|---|---|---|
| 4,686,988 A | 8/1987 | Sholder | 128/419 PT |
| 4,708,142 A | 11/1987 | DeCote, Jr. | 128/419 PT |
| 4,712,555 A | 12/1987 | Thornander et al. | 128/419 PG |
| 4,729,376 A | 3/1988 | DeCote, Jr. | 128/419 PT |
| 4,788,980 A | 12/1988 | Mann et al. | 128/419 PG |
| 4,809,697 A | 3/1989 | Causey, III et al. | 128/419 PT |
| 4,940,052 A | 7/1990 | Mann et al. | 128/419 PG |
| 4,944,298 A | 7/1990 | Sholder | 128/419 PG |
| 4,944,299 A | 7/1990 | Silvian | 128/419 PG |
| 4,969,462 A | 11/1990 | Callaghan et al. | 128/419 PG |
| 4,969,467 A | 11/1990 | Callaghan et al. | 128/419 PG |
| 5,350,410 A | 9/1994 | Kleks et al. | 607/28 |
| 5,400,795 A | 3/1995 | Murphy et al. | 128/702 |
| 5,411,533 A | 5/1995 | Dubreuil et al. | 607/28 |
| 5,417,718 A | 5/1995 | Kleks et al. | 607/28 |
| 5,466,254 A | 11/1995 | Helland | 607/123 |
| 5,476,483 A | 12/1995 | Bornzin et al. | 607/17 |
| 5,573,550 A | 11/1996 | Zadeh et al. | 607/28 |
| 5,683,431 A * | 11/1997 | Wang | 607/28 |
| 5,685,315 A | 11/1997 | McClure et al. | 128/708 |
| 5,836,984 A | 11/1998 | Obel | 607/9 |
| 5,951,593 A * | 9/1999 | Lu et al. | 607/14 |
| 6,324,427 B1 * | 11/2001 | Florio | 607/28 |
| 6,445,946 B1 * | 9/2002 | Hutten | 600/510 |
| 6,456,881 B1 * | 9/2002 | Bornzin et al. | 607/27 |

FOREIGN PATENT DOCUMENTS

| | | |
|---|---|---|
| EP | 0870516 A2 | 3/1998 |
| EP | 0870516 A3 | 3/1998 |
| EP | 0904802 A2 | 8/1998 |
| EP | 0904802 A3 | 8/1998 |
| EP | 1023919 A2 | 1/2000 |
| EP | 1023919 A3 | 1/2000 |

* cited by examiner

*Primary Examiner*—Robert E. Pezzuto
*Assistant Examiner*—Kristen Mullen

(57) ABSTRACT

An apparatus and a method for identifying fusion beats as part of an automatic capture routine in a cardiac stimulation device are disclosed. By requiring each post-pulse electrical response to be closely correlated with an expected morphology for either a capture condition or a loss-of-capture condition before classification of the post-pulse electrical response as either capture or loss-of-capture respectively, the present invention is able to identify fusion beats. In various embodiments, this fusion identification is performed using both template matching and assessment of particular detection features. Moreover, in one embodiment, a moving average and a standard deviation are maintained for each detection feature, thereby creating an automatically adjusting evoked response detection threshold.

50 Claims, 9 Drawing Sheets

METHOD AND DEVICE FOR ENHANCED CAPTURE TRACKING BY DISCRIMINATION OF FUSION BEATS

FIELD OF INVENTION

This invention relates generally to implantable cardiac stimulation devices, such as pacemakers, defibrillators, cardioverters, and combinations thereof, and more particularly, to systems and methods for identifying fusion beats in a stimulation device designed to detect capture of cardiac tissue.

BACKGROUND

A pacemaker is an implantable device that delivers electrical stimulation pulses to cardiac tissue to relieve symptoms associated with bradycardia—a condition in which a patient cannot maintain a physiologically acceptable heart rate. Early pacemakers delivered stimulation pulses at regular intervals in order to maintain a predetermined heart rate, which was typically set at a rate deemed to be appropriate for the patient at rest. The predetermined rate was usually set at the time the pacemaker was implanted, although in more advanced devices, the rate could be set remotely by a medical practitioner after implantation.

Early advances in pacemaker technology included the ability to sense intrinsic cardiac activity, i.e., the intracardiac electrogram, or "IEGM" signal. This led to the development of "demand pacemakers," so named because they deliver stimulation pulses only as needed by the heart. Demand pacemakers are capable of detecting a spontaneous cardiac contraction which occurs within a predetermined time period (commonly referred to as the "escape interval") following a preceding contraction, whether spontaneous or evoked by the implantable device. When a naturally occurring contraction is detected within the escape interval, a demand pacemaker does not deliver a pacing pulse.

Pacemakers such as those described above proved to be extremely beneficial in that they successfully reduced or eliminated seriously debilitating and potentially lethal effects of bradycardia in many patients. However, since pacemakers are implantable devices, an invasive surgical procedure is required, and many patients who receive pacemakers must undergo several surgical procedures, because pacemakers have a limited life span, due to limited battery life, and therefore require periodic replacement. Of course, it is desirable to minimize the number of surgical procedures that must be performed on a patient to improve safety and reduce costs, not to mention patient inconvenience and discomfort.

The life span of most pacemakers is directly related to the rate at which their batteries drain. Thus, a substantial effort has been directed toward minimizing the amount of energy used by pacemakers, while ensuring that the devices continue to deliver effective therapy. Demand pacemakers effectively reduce battery drain by delivering pacing pulses only when required. However, each pacing pulse delivered by a demand pacemaker may have a significantly higher energy content than that required for inducing a cardiac contraction. Thus, even after the development of demand pacemakers, there remained an opportunity for further improvements in the area of pacemaker energy utilization.

The minimum amount of electrical stimulation that effectively evokes a cardiac contraction is commonly referred to as a patient's "capture threshold." Unfortunately, capture threshold varies significantly among patients; therefore, the amount of electrical stimulation provided by a pacemaker cannot be permanently set by the manufacturer. Rather, stimulus parameters must be individually set for each patient immediately after implantation and during subsequent office visits.

Determining a particular patient's capture threshold is a relatively simple procedure when performed during an office visit. Essentially, the medical practitioner can remotely adjust the amount of electrical stimulation downward from a maximum value that is known to elicit a contraction for all patients. Once the amount of electrical stimulation falls below the patient's capture threshold, an ensuing heartbeat is not detected, and the medical practitioner increases the amount of electrical stimulation beyond the last successful level.

Typically, a substantial safety margin is added to the measured capture threshold to ensure that the pacemaker continues to evoke contractions over an extended period of time. The safety margin is necessary because a patient's capture threshold varies over time—sometimes dramatically during the first few months following implantation. However, by adding such a large safety margin, it is almost assured that the pacemaker will be wasting significant amounts of energy during its life span.

In an effort to reduce the amount of energy wasted, pacemakers have been developed that periodically (or even continually) evaluate the patient's capture threshold during normal operation. These devices are also capable of automatically adjusting the amount of electrical stimulation in response to changes to the capture threshold. These features, which in combination are referred to herein as "automatic capture detection", significantly reduce unnecessary battery drain, because higher energy pacing pulses are delivered only when needed by the patient. Although most of these devices continue to add a safety margin to the measured capture threshold, the safety margin can be greatly reduced, especially when the capture threshold is measured frequently.

Pacemakers that perform automatic capture detection commonly monitor a patient's IEGM signal to determine what pulsing energy level is necessary to evoke a responsive cardiac contraction ("evoked response"). In particular, the pacemaker samples the portion of the patient's IEGM signal corresponding to the evoked response, if any, immediately after a pacing pulse is delivered. The shape of the waveform indicates whether the pacing pulse successfully captured the heart. However, known automatic capture detection methods have several drawbacks, particularly relating to signal processing, which have proven difficult to overcome. For example, it is extremely difficult to accurately sense the evoked response immediately after a pacing pulse is delivered, due to the presence of residual electrical effects in the immediate vicinity of the pacing electrodes. These residual effects (commonly known as "polarization") interfere with the pacemaker's ability to sense the evoked response. Indeed, most pacemakers enter a refractory period immediately after a pacing pulse is delivered, during which time the sensing circuitry is deactivated, for the specific purpose of avoiding undesirable sensing of polarization.

One automatic capture system and method is described in U.S. Pat. No. 5,350,410 ('410 patent) entitled "Autocapture System for Implantable Pulse Generator" (Kleks et al.), which is hereby incorporated by reference as if set forth fully herein. The '410 patent discloses a capture verification test for determining the polarization template and which sensitivity settings yield capture. In addition, the '410 patent also discloses an auto-threshold routine for automatically setting the output energy of the normal stimulation pulse. Thus, typical capture tracking systems allow reduced power usage for implantable pacemakers and ICDs, without compromising patient safety.

Traditional capture tracking systems, however, fail to identify fusion beats. A fusion beat is a cardiac depolarization (either atrial or ventricular) that results from two foci. In pacing, a fusion beat typically refers to the electrocardiogram ("ECG" or "EKG") waveform which results when an intrinsic depolarization and a pulse generator output pulse occur simultaneously (or nearly simultaneously), and both contribute to the electrical activation of the heart chamber. A pseudofusion beat is a spontaneous cardiac depolarization occurring simultaneously (or nearly simultaneously) with a pulse generator output pulse, where the output pulse does not contribute to the cardiac depolarization but nonetheless distorts the morphology of the waveform on the ECG. A pseudopseudofusion beat is an electrocardiographic superimposition of an atrial stimulus on a native QRS complex in a ventricle. Hereinafter, fusion beats, pseudofusion beats and pseudopseudofusion beats are referred to collectively as "fusion beats."

Because conventional capture tracking systems do not identify fusion beats, these occurrences are typically treated as loss of capture. If a capture tracking system cannot positively identify a sensed signal as capture, loss of capture is assumed in order to guarantee patient safety. But this approach to pacing causes the capture tracking system to routinely issue unnecessary backup pulses, initiate unnecessary threshold searches, and possibly find incorrect capture threshold pulse energies. These problems are particularly pronounced in patients who have atrial fibrillation.

Some have suggested a modification to traditional capture tracking systems and methods, whereby fusion beats may be avoided. In this modification, the escape interval is increased slightly for the next cardiac cycle after a loss of capture event. If a spontaneous cardiac depolarization is then detected before the elongated escape interval, this indicates that the prior loss of capture event was likely due to fusion activity. Thus, the escape interval is maintained at the longer time period until a spontaneous depolarization does not occur in time, at which point the escape interval is reduced to its programmed length.

This modification of a capture tracking system helps to avoid treatment of fusion activity as loss of capture, particularly in devices using dual chamber sensing. It does not, however, eliminate the existing problems in the art. Even with this modification of a capture tracking system, unnecessary backup pulses may still be issued, unnecessary threshold searches may be initiated, and incorrect capture threshold pulse energies may be found. Moreover, because all loss of capture events are assumed to be potential fusion beats, the modification is employed unnecessarily at times.

SUMMARY OF THE INVENTION

The present invention is directed to improving stimulation device performance by teaching a method and apparatus for identifying fusion beats in cardiac tissue. In one embodiment, the invention comprises a method of identifying fusion beats during a capture detection process used in delivering pacing pulses to a heart. A post-pulse electrical response is sensed, and the resulting signal is assessed with a capture detection function. If the capture detection function fails to confirm capture, the post-pulse electrical response is assessed with a loss-of-capture detection function. If the loss-of-capture detection function fails to confirm loss-of-capture, the post-pulse electrical response is classified as a fusion beat.

In one embodiment, the capture detection function and the loss-of-capture detection function utilize one or more detection features for the post-pulse electrical response. The available detection features include, by way of example, a paced depolarization integral ("PDI"), a peak negative amplitude, a peak amplitude, a maximum positive slope ("DMAX"), positive or negative integrals, time of peaks, time of zero crossings, and the like, as well as combinations of these and other such features. In this embodiment, the method further includes comparing a computed value for the detection feature with a first evoked response sense level threshold, and comparing the computed value with a second evoked response sense level threshold.

The first evoked response sense level threshold comprises the lower limit of those values for the detection feature that are classified as capture. In one embodiment, this classification is based upon a moving average and standard deviation for the detection feature. The second evoked response sense level threshold comprises the upper limit of those values for the detection feature that are classified as loss-of-capture. In one embodiment, this upper limit is set halfway between the maximum value for the detection feature for a set of polarization signals and the mean value for the detection feature for a set of evoked response signals.

In an alternative embodiment, the capture detection function and the loss-of-capture detection function utilize signal recognition templates to classify the post-pulse electrical response. The capture detection function creates a capture correlation coefficient by comparing the post-pulse electrical response with an evoked response signal recognition template using a simple point-by-point subtraction. The loss-of-capture detection function creates a loss-of-capture correlation coefficient by comparing the post-pulse electrical response with a polarization signal recognition template using R-squared correlation. If the capture correlation coefficient and the loss-of-capture correlation coefficient are both insufficient to confirm a state of capture or loss-of-capture, the post-pulse electrical response is classified as a fusion beat, no backup pulse is necessary, and fusion avoidance mechanisms can be employed.

This invention can also be regarded as an apparatus and a method for identifying fusion beats with an automatically adjusting evoked response threshold as part of an automatic capture tracking routine in a cardiac stimulation device. The method includes the step of computing a value for a detection feature of a post-pulse electrical response. The available detection features include, by way of example, a paced depolarization integral, a peak negative amplitude, a peak amplitude, a maximum positive slope, positive or negative integrals, time of peaks, time of zero crossings, and the like, as well as combinations of these and other such features. The method further includes the step of classifying the post-pulse electrical response as a fusion beat if the value falls outside a prescribed deviation and not within a loss-of-capture range specified by an evoked response sense level threshold, wherein the prescribed deviation is determined using a moving average and a standard deviation (or other measure of variance) for the detection feature. Finally, the method includes the step of recalculating the moving average and the standard deviation using the value of the detection feature for the post-pulse electrical response if the value falls within the prescribed deviation.

In one embodiment, the prescribed deviation comprises a first deviation and a second deviation. If the value falls above the first deviation, the post-pulse electrical response is immediately classified as a fusion beat, thereby avoiding additional processing time. If the value falls below the second deviation and above the evoked response sense level threshold, the post-pulse electrical response is also classified as a fusion beat. In one embodiment, the first deviation, the second deviation and the evoked response sense level threshold are separately programmable.

Further features and advantages of the invention as well as the structure and operation of various embodiments of the invention are described in detail below with reference to the accompanying drawings.

BRIEF DESCRIPTION OF FIGURES

The features and advantages of the present invention may be more readily understood by reference to the following description, taken in conjunction with the accompanying drawings, in which.

DETAILED DESCRIPTION OF INVENTION

The present invention is directed toward a system and method for enhancing performance of an implantable stimulation device by discrimination of fusion beats. The following description is of various embodiments of the invention, including the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
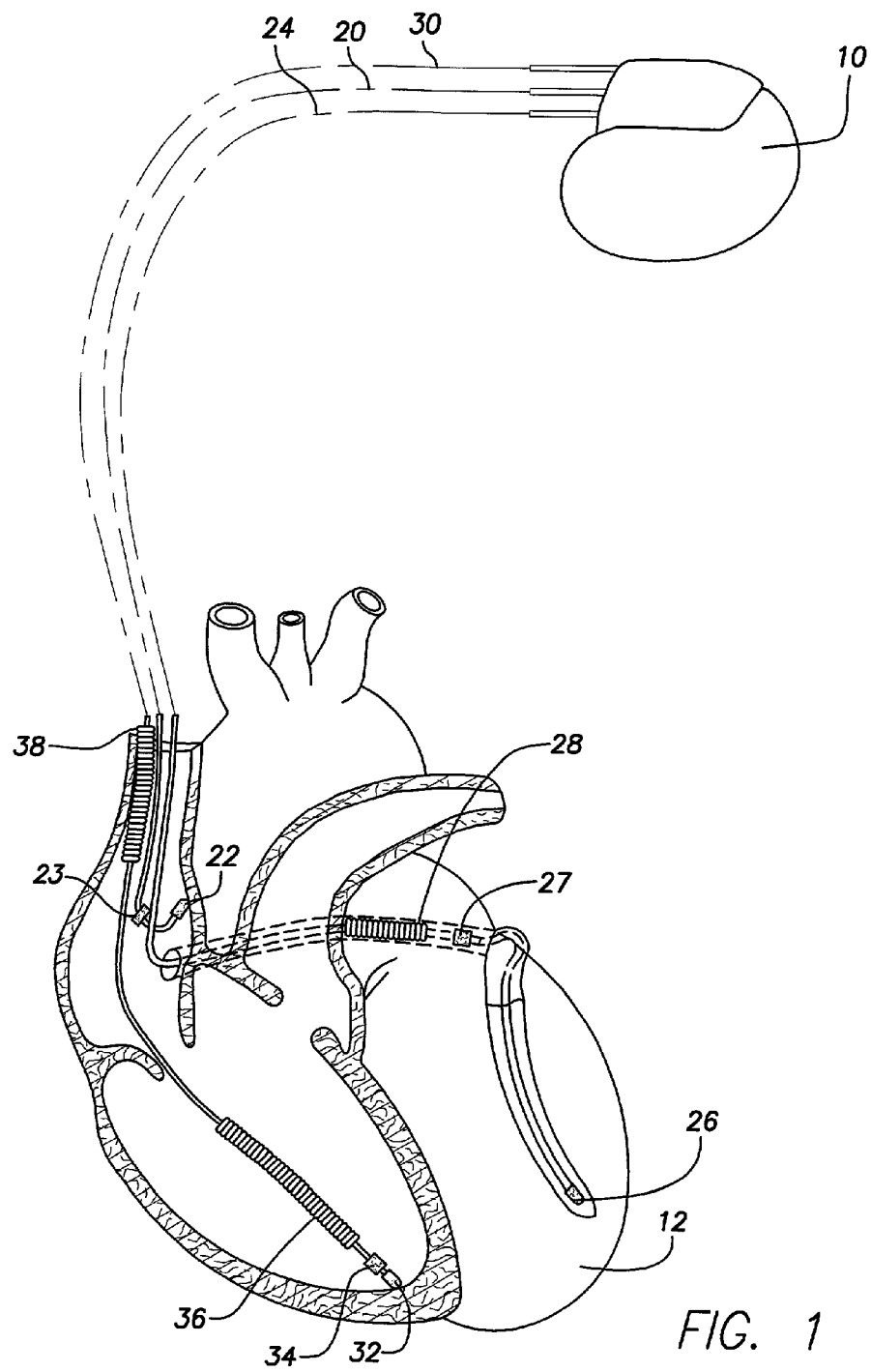
FIG. 1 is a diagram illustrating an implantable stimulation device in electrical communication with three leads implanted into a patient's heart for delivering multi-chamber stimulation and shock therapy according to one embodiment of the invention.

FIG. 1 is a diagram illustrating an implantable stimulation device in electrical communication with three leads implanted into a patient's heart for delivering multi-chamber stimulation and shock therapy according to one embodiment of the invention. The present invention may be used with as few as one lead and may be used for pacing any of the four chambers of the heart. The number of leads used, and the location(s) of attachment to the heart, will depend on the particular patient's condition, as is well known in the relevant art(s). For example, in one dual-chamber pacing embodiment, the implantable stimulation device includes two leads that are adapted to be positioned within the right atrium and the right ventricle of the heart respectively, so as to enable delivery of pacing pulses and sensing of heart activity in both the right atrium and right ventricle. It will also be understood that the electrodes used to pace and sense may be the same electrodes, or different electrodes on the respective leads.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having an atrial tip electrode 22, which typically is implanted in the patient's right atrial appendage. Moreover, the implantable right atrial lead 20 includes an atrial ring electrode 23 located relatively near the atrial tip electrode 22. This proximity enables localized bipolar sensing of an evoked response within the right atrium of the heart 12, thereby reducing sensing of extraneous myopotentials, as is well understood in the art. In addition, this proximity enables sensing of an evoked response with the atrial ring electrode 23. In one embodiment, at least one electrode used in the sensing vector is located relatively close to the electrode used to deliver the stimulation pulse, or may be the same electrode used to deliver the pacing pulse. However, the electrode(s) used to sense may vary, as is well known in the art.

In one embodiment, each electrode used for both delivery of stimulation pulses and sensing of evoked responses is designed to reduce polarization on the electrode. Such polarization reducing designs include increased surface geometry and specialized electrode coatings, as is well known in the art.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using a left atrial ring electrode 27, and shocking therapy using at least a left atrial coil electrode 28. For a complete description of a coronary sinus lead, see U.S. patent application Ser. No. 09/457,277, filed Dec. 8, 1999, entitled "A Self-Anchoring, Steerable Coronary Sinus Lead" (Pianca et al.); and U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. The right ventricular ring electrode 34 is located relatively near the right ventricular tip electrode 32. This proximity enables localized bipolar sensing of an evoked response within the right ventricle of the heart 12, thereby reducing sensing of extraneous myopotentials, as is well understood in the art. In addition, this proximity enables sensing of an evoked response with the right ventricular ring electrode 34. In one embodiment, at least one electrode used in the sensing vector is located relatively close to the electrode used to deliver the stimulation pulse, or may be the same electrode used to deliver the pacing pulse. However, the electrode(s) used to sense may vary, as is well known in the art.

Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
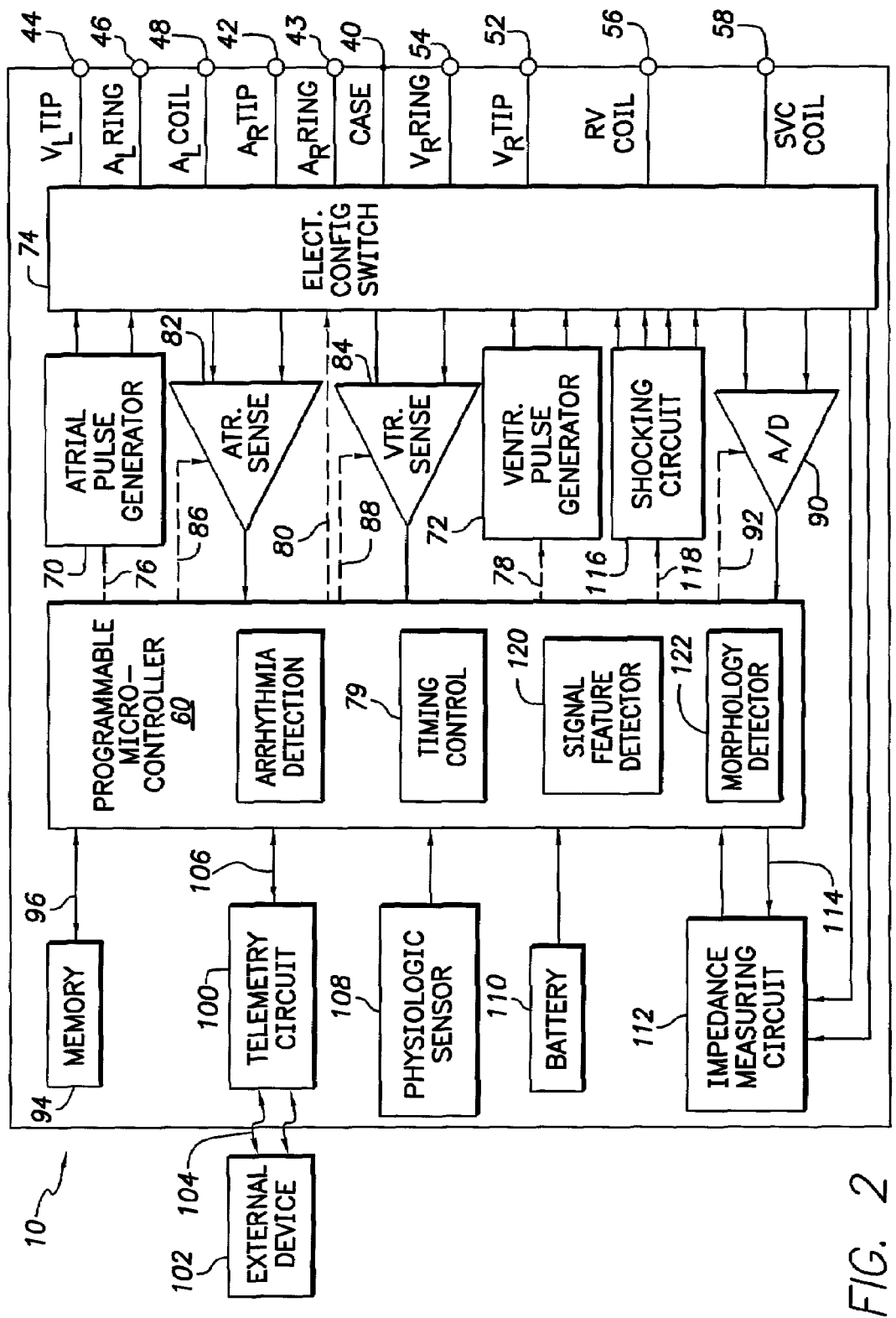
FIG. 2 is a functional block diagram of a multi-chamber implantable stimulation device illustrating the basic elements of a stimulation device that can provide cardioversion, defibrillation and pacing stimulation in multiple chambers of the heart according to one embodiment of the invention.

FIG. 2 is a functional block diagram of a multi-chamber implantable stimulation device illustrating the basic elements of a stimulation device which can provide cardioversion, defibrillation and pacing stimulation in four chambers of the heart according to one embodiment. As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and/or pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 43, 44, 46, 48, 52, 54, 56, and 58 (shown schematically and, for convenience, the names of the electrodes to which they are connected are shown next to the terminals). As such, to achieve right atrial sensing and pacing, the connector includes a right atrial tip terminal ($A_R$ TIP) 42 adapted for connection to the atrial tip electrode 22 and a right atrial ring terminal ($A_R$ RING) 43 adapted for connection to the atrial ring electrode 23.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

Representative types of control circuitry that may be used with the invention include the microprocessor-based control system of U.S. Pat. No. 4,940,052, entitled "Microprocessor Controlled Rate-responsive Pacemaker Having Automatic Rate Response Threshold Adjustment" (Mann et al.), the state-machine of U.S. Pat. No. 4,712,555, entitled "Physiologically Responsive Pacemaker and Method of Adjusting the Pacing Interval Thereof" (Thornander et al.), and U.S. Pat. No. 4,944,298, entitled "Atrial Rate Based Programmable Pacemaker with Automatic Mode Switching Means" (Sholder). For a more detailed description of the various timing intervals used within the stimulation device and their inter-relationship, see U.S. Pat. No. 4,788,980, entitled "Pacemaker Having PVC Response and PMT Terminating Features" (Mann et al.). The '052, '555, '298 and '980 patents are hereby incorporated herein by reference.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity. Moreover, in one embodiment, the switch 74 includes at least one small resistor for electrically connecting a lead electrode, which has been used to deliver a stimulation pulse, with the case 40, thereby enabling rapid reduction of polarization on the stimulation electrode prior to using that same electrode for sensing evoked response.

In one embodiment, each sensing circuit, 82 and 84, employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing low amplitude signal characteristics of atrial or ventricular fibrillation.

For a complete description of a typical sensing circuit, see U.S. Pat. No. 5,573,550, entitled "Implantable Stimulation Device having a Low Noise, Low Power, Precision Amplifier for Amplifying Cardiac Signals" (Zadeh et al.). For a complete description of an automatic gain control system, see U.S. Pat. No. 5,685,315, entitled "Cardiac Arrhythmia Detection System for an Implantable Stimulation Device" (McClure et al.). Accordingly, the '550 and the '315 patents are hereby incorporated herein by reference.

The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

In one embodiment, the data acquisition system 90 is coupled with the microcontroller 60, and/or other detection circuitry, for detecting an evoked response and/or a lead polarization signal from the heart 12 in response to an applied stimulus, thereby aiding in the detection of "capture" and "loss-of-capture" (LOC). In an alternative embodiment, the data acquisition system 90 is built into the microcontroller 60, whereby digital signals representative of cardiac activity are generated by a control program designed to sample atrial and/or ventricular cardiac signals acquired by the atrial and ventricular sensing circuits, 82 and 84.

Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that cardiac contraction has begun. In one embodiment, the microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on a detection feature, such as the amplitude of the sensed signal, determines if capture has occurred.

Capture detection may occur on a beat-by-beat basis or on a sampled basis. In one embodiment, a capture threshold search is performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold to define the pacing level.

The implementation of capture detection circuitry and algorithms are well known. See, for example, U.S. Pat. No. 4,729,376, entitled "Cardiac Pacer and Method Providing Means for Periodically Determining Capture Threshold and Adjusting Pulse Output Level Accordingly" (Decote, Jr.); U.S. Pat. No. 4,708,142, entitled "Automatic Cardiac Capture Threshold Determination System and Method" (Decote, Jr.); U.S. Pat. No. 4,686,988, entitled "Pacemaker System and Method for Measuring and Monitoring Cardiac Activity and for Determining and Maintaining Capture" (Sholder); and U.S. Pat. No. 4,969,467, entitled "Pacemaker with Improved Automatic Output Regulation" (Callaghan et al.). The '376, '142, '988, and '467 patents are hereby incorporated herein by reference.

As will be described in greater detail below, the stimulation device 10 is adapted to be able to identify fusion beats within the heart 12, thereby enabling the stimulation device 10 to operate in a more efficient manner. It will be appreciated from the following discussion that the manner in which the stimulation device 10 identifies fusion beats can be used in any of a number of different implantable cardiac stimulation devices without departing from the spirit of the present invention.

The microcontroller 60 is further coupled to a memory 94 by a suitable data/address bus 96. The microcontroller 60 uses the memory 94 for storage of control data used in controlling the operation of the stimulation device 10. The control data comprises programmable operating parameters, which can be stored and modified, as needed, to customize the operation of the stimulation device 10 for a particular patient. Such operating parameters include, for example, pacing pulse amplitude, pulse duration, electrode polarity, rate, sensitivity, signal sampling, automatic features, arrhythmia detection criteria, and the amplitude, waveshape and vector of each shocking pulse to be delivered to the patient's heart 12 within each respective tier of therapy.

The microcontroller 60 also uses the memory 94 for periodic recording of historical data acquired by the data acquisition system 90. This historical data comprises both patient data and device data. Thus a treating physician may use this historical data to review the performance of the implanted stimulation device 10 and the function of the heart 12 during follow-up visits. This historical data may also be used for subsequent analysis to guide the programming of the stimulation device 10, either by a human programmer or by the stimulation device 10 itself.

Advantageously, the historical data may be non-invasively downloaded from memory 94 and the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. Examples of this established communication link 104 include an electromagnetic telemetry link and a remote communication link such as a pair of modems interconnected via a telecommunications link and equipped with telemetry capabilities.

In alternative embodiments, the stimulation device 10 includes one or more physiologic sensors 108, such as activity sensors, minute ventilation sensors, and the like. These physiologic sensors 108 are commonly referred to as "rate-responsive" sensors because they are typically used to adjust pacing stimulation rate according to the exercise state of the patient. However, the physiological sensors 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

While shown as being included within the stimulation device 10, it is to be understood that the physiologic sensors 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. However, any sensor may be used which is capable of sensing a physiological parameter which corresponds to the exercise state of the patient. The type of sensor used is not critical to the present invention and is shown only for completeness.

The stimulation device additionally includes a battery 110 which provides operating power to all of the circuits shown in FIG. 2. In one shock-therapy embodiment of the stimulation device 10, the battery 110 is capable of operating at low current drains for long periods of time, and of providing high-current pulses (for capacitor charging) when the patient requires a shock pulse. In this embodiment, the battery 110 also has a predictable discharge characteristic so that elective replacement time can be detected. Accordingly, in one embodiment, the device 10 employs lithium/silver vanadium oxide batteries, as is true for most (if not all) current devices.

In one embodiment, the stimulation device 10 further includes magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

In another alternative embodiment, the device 10 includes an impedance measuring circuit 112, which is enabled by the microcontroller 60 via a control signal 114. The known uses for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used. The impedance measuring circuit 112 is not critical to the present invention and is shown only for sake of completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV coil electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

The operation of the stimulation device 10 is generally controlled by a control program stored in the memory 94 and executed by the microcontroller 60. In one embodiment, this control program comprises multiple integrated program modules, with each module bearing responsibility for controlling one or more functions of the stimulation device 10. For example, one program module may control the delivery of stimulating pulses to the heart 12, while another may control the verification of ventricular capture and the determination of ventricular pacing energy output. As shown, the capture verification module may include a signal feature detector module 120 and a morphology detector module 122. In effect, each program module is a control program dedicated to a specific function or set of functions of the stimulation device 10.

Figure 3:
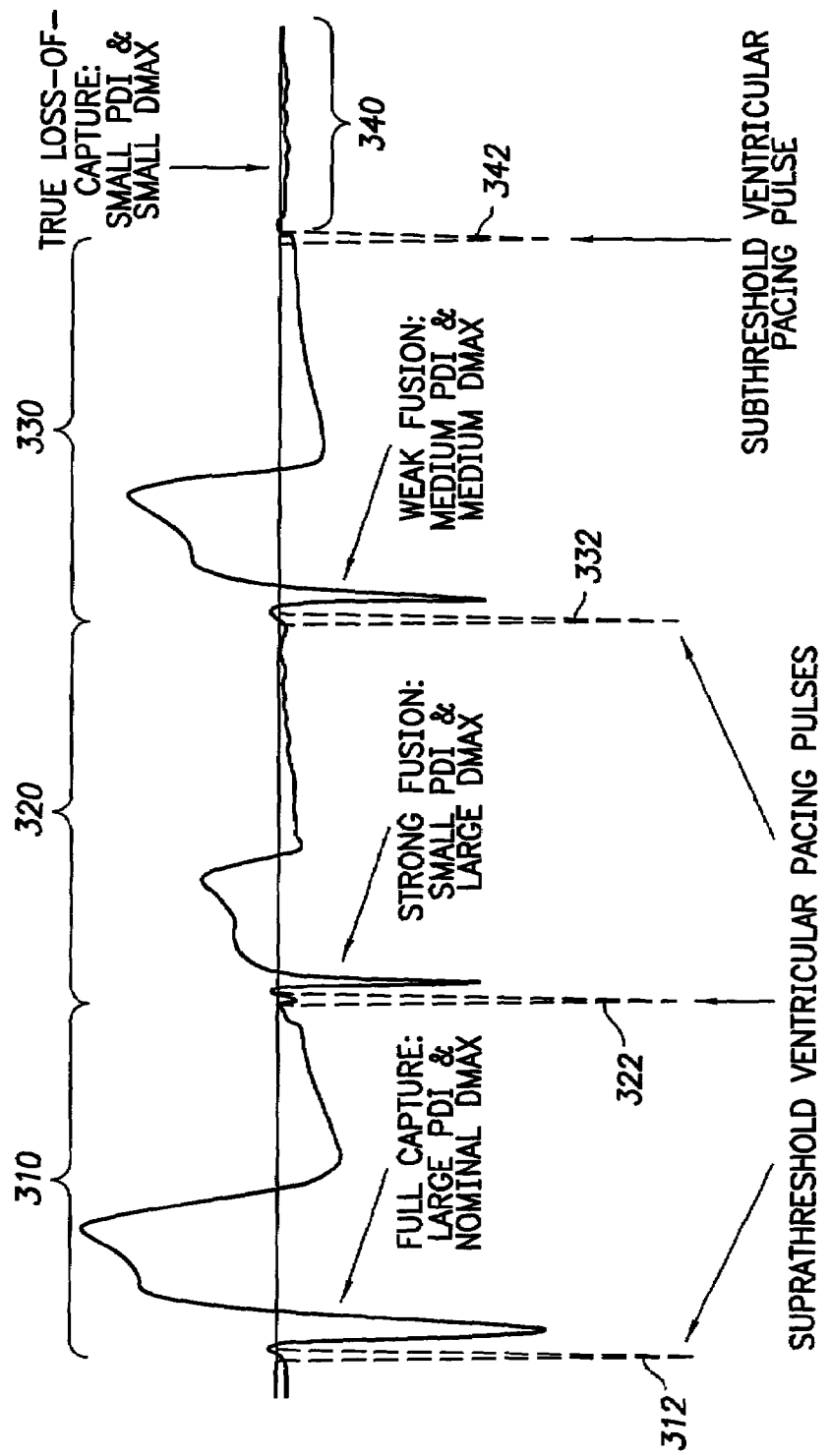
FIG. 3 is an illustration of exemplary signals detected by a stimulation device, wherein the signals represent a capture condition, two fusion beat conditions and a loss-of-capture condition.

FIG. 3 is an illustration of exemplary signals detected by a stimulation device, wherein the signals represent a capture condition, a fusion beat condition and a loss-of-capture condition. In FIG. 3, four exemplary signals representing four sensed responses to a pacing pulse are shown. A first signal 310 represents an evoked response following a first ventricular pacing pulse 312. The first ventricular pacing pulse 312 was above the capture threshold and no spontaneous depolarization has occurred. Thus the first signal 310 shows the general morphology of full capture. This full capture signal 310 is generally characterized by a large PDI (paced depolarization integral) and a nominal DMAX (maximum positive slope).

A second signal 320 represents an evoked response following a second ventricular pacing pulse 322. The second ventricular pacing pulse 322 was above the capture threshold, but the second pulse 322 coincided with a spontaneous depolarization with the propagation wave of an intrinsic depolarization very close to the electrode. This morphology may be defined as "strong fusion". Thus the second signal 320 shows the general morphology of the evoked response in the presence of strong fusion. This strong fusion signal 320 is generally characterized by a small PDI and a large DMAX.

A third signal 330 represents an evoked response following a third ventricular pacing pulse 332. As in the case of strong fusion, the third ventricular pacing pulse 332 was above the capture threshold, but the third pulse 332 coincided with a spontaneous depolarization of the ventricle. In this case, the wave of intrinsic depolarization and propagation was further from the electrode at the time of delivery of the pacing pulse. This may be defined as "weak fusion". Thus the third signal 330 shows the general morphology of capture in the presence of weak fusion. This weak fusion signal 330 is generally characterized by a medium PDI and a medium DMAX.

A fourth signal 340 represents a sensed response following a fourth ventricular pacing pulse 342. The fourth ventricular pacing pulse 342 was below the capture threshold and no spontaneous depolarization occurred. Thus the fourth signal 340 shows the general morphology of a loss-of-capture (i.e. a polarization signal). This polarization signal 340 is generally characterized by a small PDI and a small DMAX.

Figure 4A:
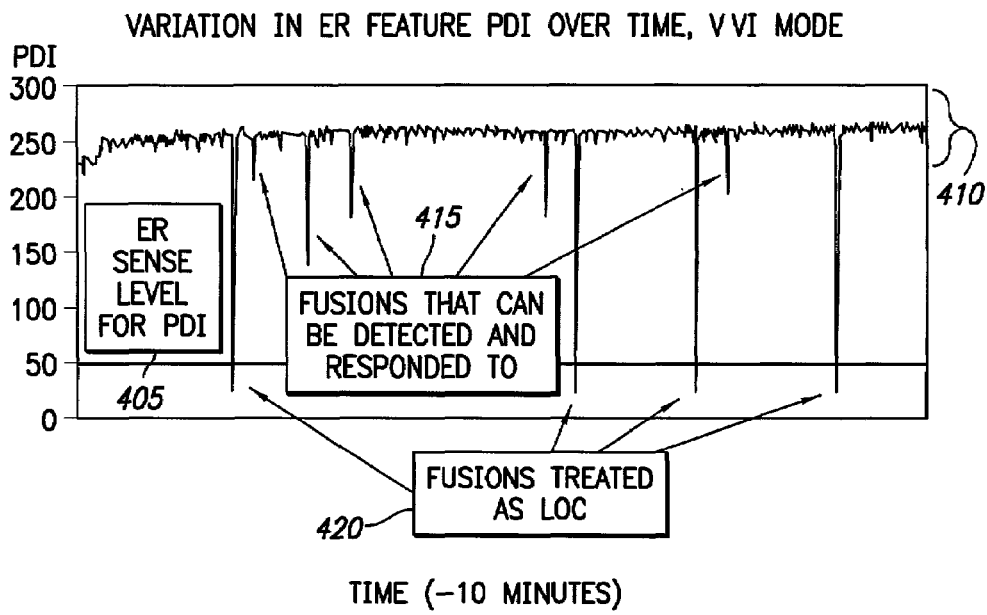
FIG. 4A is an illustration of an exemplary paced depolarization integral detection feature used by an implantable stimulation device according to one embodiment of the invention.

FIG. 4A is an illustration of an exemplary paced depolarization integral detection feature used by an implantable stimulation device according to one embodiment. FIG. 4A shows the paced depolarization integral (PDI) signal feature measured in a canine over a short period of time in a near-overdrive WI mode with the pacing voltage above the capture threshold. For most of the time, the feature value is very stable. This stable PDI value indicates consistent capture. Occasionally, the PDI feature value deviates significantly from the normal value. These deviations indicate the presence of either a fusion beat or a loss-of-capture.

With a low-polarizing lead, the PDI feature value for loss-of-capture is very small. However, for safety reasons, an ER sense level 405 is programmed with a significant safety margin, putting it somewhere between the mean ER value and the maximum POL value. For example, the ER sense level 405 may be programmed at a level corresponding to 50% of the difference between the mean ER value and the maximum POL value. As shown, the stable PDI feature value stays within the range 410, thereby indicating capture. The fusion beats 415 and 420, have PDI feature values that deviate from this range 410. Due to the safety margin built into the ER sense level 405, the fusion beats 415 can be detected and responded to as fusion beats, but the fusion beats 420 are treated as loss-of-capture. It will be understood that the ER sense level 405 can be set to a higher level to detect more of the fusion beats.

In addition to PDI, many alternative detection signal features are available. For example, signal features such as the peak negative amplitude of the unipolar ER, peak amplitude, peak slope, positive or negative integral, time of peaks, and time of zero crossings may be used, as well as combinations of these. Each such detection feature has its own particular pattern, which is readily ascertainable by those skilled in the art. The difference in patterns can be used to create more robust fusion detection. For example, in one embodiment, the PDI feature is combined with the maximum positive slope (DMAX). In this embodiment, the PDI feature is used as the ER detection feature and a fusion detection feature, while the DMAX feature is used solely as a fusion detection feature to back up the PDI measurement.

Figure 4B:
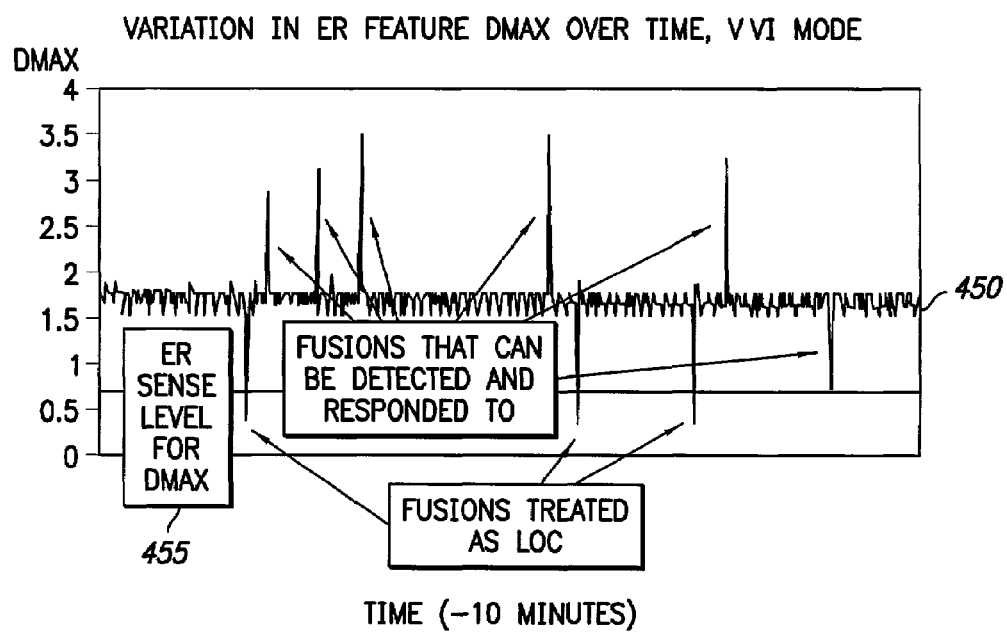
FIG. 4B is an illustration of an exemplary maximum positive slope detection feature used by an implantable stimulation device according to one embodiment of the invention.

FIG. 4B is an illustration of an exemplary maximum positive slope detection feature used by an implantable stimulation device according to one embodiment. FIG. 4B shows the DMAX signal feature measured in a canine over a short period of time in a near-overdrive WI mode with the pacing voltage above the capture threshold. For most of the time, the feature value is very stable around the mean DMAX 450. This stable DMAX value indicates consistent capture. Occasionally, the DMAX feature value deviates significantly from the normal value. These deviations indicate the presence of either a fusion beat or a loss-of-capture.

It should be noted that unlike the PDI feature values, the significant deviations of the DMAX feature value go both above and below the mean DMAX 450. This is because the intrinsic R-wave and many fusion beats often have higher slope values than the standard unipolar ventricular evoked response ($V_{ER}$). Thus, the DMAX feature values that deviate significantly above the mean DMAX 450 can be instantly identified as fusion beats. Those that deviate significantly below the mean DMAX 450, however, may or may not correspond to fusion beats, and may be characterized by relying on the ER sense level value 455.

Figure 5:
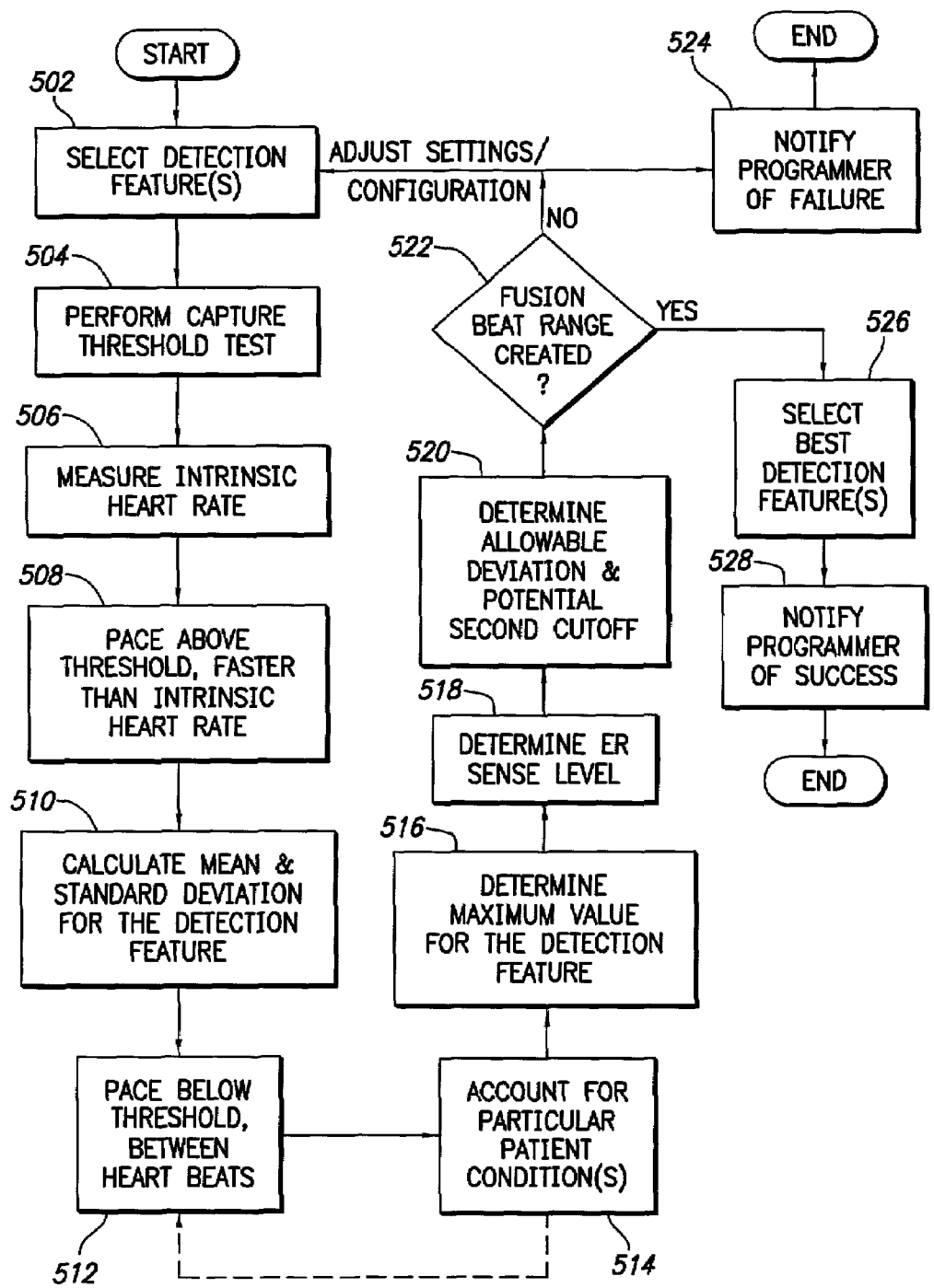
FIG. 5 is a logic flow diagram of a calibrating control program executed by a microcontroller in an implantable stimulation device according to one embodiment of the invention.

FIG. 5 is a logic flow diagram of a calibrating control program executed by a microcontroller in an implantable stimulation device according to one embodiment of the invention. The control program is used to select one or more detection features as the parameters to be monitored. The logic flow diagram of FIG. 5 represents an overview of the operation and novel features of one aspect of one embodiment of the stimulation device 10. In this flow chart, and the other flow charts described herein, the various algorithmic steps are summarized in individual "blocks." Such blocks describe specific actions or decisions that are carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

Referring now to FIG. 5, the calibrating process begins with step 502, in which one or more detection features are selected. This selection may be performed by a programmer of the stimulation device, or by the device itself. In one embodiment, the stimulation device performs the calibration process for multiple detection features and then selects the best detection feature, or combination of features, at the end of the calibration process. Examples of available detection features include signal features such as the peak negative amplitude of the unipolar ER, peak amplitude, peak slope, positive or negative integral, time of peaks, time of zero crossings, and the like, as well as combinations of these and other such features.

Following step 502, a capture threshold test is performed in step 504. This capture threshold test identifies the patient's current capture threshold. Then in step 506, the patient's current intrinsic heart rate is measured. For patients who require regular pacing therapy, such as those with complete heart block, step 506 may be unnecessary.

Following the determination of capture threshold and intrinsic heart rate, the patient's heart is paced at a voltage level above the capture threshold (e.g., on the order of 0.5V or greater), at a rate higher than the patient's intrinsic heart rate (e.g., on the order of 10–20 beats per minute above the intrinsic rate), in step 508. This pacing step 508 ensures that the measured evoked responses are true evoked responses, which are not affected by fusion activity. During this pacing step 508, a detection feature value for each selected detection feature is determined and stored for each sensed signal.

In one embodiment, the voltage level is varied during step 508 to cover a number of output levels, each of which is above the capture threshold. This is done to ensure that the measured detection features cover a wide range of applied pulse energies. Generally, however, this variation is not needed. Although the ER signal does change with posture, stress, and other variables that affect intracellular and extracellular ionic balance and tissue conduction velocity, it is consistent enough for reliability. The ER signal has a relatively unchanging distinct morphology and relatively unchanging amplitude across different stimulation output energies, provided that actual capture of the heart is effected. Thus, the variations in the measured detection features caused by variations in applied energy levels are minimal. This alternative embodiment may be used to add an additional safety measure.

In step 510, a measure of average value (e.g., the mean) and a measure of statistical distribution (e.g., the standard deviation) are calculated for the stored feature values (obtained during overdrive capture) for each selected detection feature. Then, in step 512, the patient's heart is paced below the identified capture threshold. For example, in one embodiment, stimulation pulses equal to half the capture threshold are delivered to the patient's heart in between the normal heart beats. The signals sensed following the sub-threshold pulses are the POL signals (i.e., the charge remaining on the electrodes), and for each such POL signal, a detection feature value is determined and stored for each selected detection feature.

Following step 512, the patient's particular condition is accounted for in step 514. This may be a single step after multiple pacing pulses, or it may be a step that is repeated with step 512 for each pacing pulse. For example, for patients with complete heart block, the patient's heart is paced with paired pulses. On the primary pulse, the patient's heart is paced at half the capture threshold voltage to get the data in step 512, and after each such pulse, the patient's heart is stimulated with a second, suprathreshold pulse to ensure that the chamber contracts.

In one embodiment, the pulses delivered in step 512 are varied in terms of output energy. Because the POL signal varies in amplitude with the output energy of the stimulation pulse, certain stored detection feature values need to be adjusted by a scaling factor. Studies have shown that features of the polarization artifact are highly linearly related to the pulse output energy. Thus, the scaling factor may be calculated directly using a present sensitivity setting and electrode configuration along with known properties of the electrodes being used. The output energy variations performed in step 512 are done to double check this scaling factor.

In an alternative embodiment, the output energy is varied in step 512, but no scaling factor is used. In this embodiment, it is advantageous to have at least one of the pacing pulses delivered in step 512 be at an energy level very close to but below the capture threshold, thereby ensuring that a maximum detection feature value is obtained.

Following step 514, the maximum stored value for each detection feature is determined in step 516. Then in step 518, an ER sense level is determined for each selected detection feature. In one embodiment, the ER sense level is determined by calculating a sense level threshold equal to one half the sum of the mean value for the stored detection feature values for the ER signals and the maximum stored value for the detection feature for the POL signals. This is referred to herein as a "50% of the difference" level. Any values below that level are classified as loss-of-capture events.

Then, in step 520, an allowable deviation and a potential second cutoff are determined. The allowable deviation is a range around the mean value for a detection feature, such that a value measured in the future for that same detection feature, which falls into the range, will be determined to be an indication of a true evoked response. This range is defined by a number N (not confined to integer values), which corresponds to the number of standard deviations around the mean value for the detection feature. This number N is fully programmable, defaults to the number three, and, in one embodiment, is limited to the range of three to eight. This range defines a lower cutoff threshold equal to the mean value minus N times the standard deviation for each detection feature. Any measure detection feature value below this lower cutoff threshold is either indicative of a loss-of-capture or a fusion beat.

The potential second cutoff is determined in step 520 only if the selected detection feature can utilize it. For example, as discussed previously, the DMAX detection feature has the property that any measured DMAX value that is greater than the mean DMAX plus N times the standard deviation for the DMAX is automatically classified as a fusion beat. This upper cutoff for the DMAX detection feature represents a second cutoff determined in step 520. In one embodiment, the lower cutoff threshold and the potential upper cutoff are separately programmable.

In step 522, the lower cutoff threshold is compared with the ER sense level for each selected detection feature to determine if an adequate fusion beat range has been created. In one embodiment, the adequate fusion beat range is defined generally by a lower cutoff threshold that is at least ten percent greater than the ER sense level, however, the adequate fusion beat range is also dependent on the accuracy and the precision of the sensing mechanism.

If none of the selected detection features has an adequate fusion beat range, control passes to step 524, in which the programmer and/or attending physician are notified of the failure. As shown, the process ends following step 524. In practice, however, the programmer may adjust the sensitivity settings and/or the sensing electrode configurations following step 524, then initiate the calibrating process again.

In addition, in one embodiment, the control program for the stimulating device automatically performs these adjustments. In this embodiment, steps 502 through 522 represent a loop in which multiple sensitivity settings and multiple sensing electrode configurations are tried by the stimulating device before a failure is reported in step 524. One such automatically adjusting calibration embodiment is designed to obtain the best configuration for sensing the polarization artifact. This configuration provides a consistent detection feature for the sensed POL signal that is maximally different from the same detection feature for the ER signal.

If at least one of the selected detection features has an adequate fusion beat range in step 522, control passes to step 526. In step 526, the best detection feature or features are selected based upon the determination made in step 522.

Following step 526, the programmer and/or the attending physician is notified of the success of the calibration routine in step 528, before the process ends. In one embodiment, this calibration process is performed at implant, prior to discharge of the patient from the hospital, and during follow-up visits to ensure patient safety. Moreover, in an alternative embodiment, this calibration process is performed for multiple states, such as time of day, level of activity, etc., to obtain multiple sets of ER sense level, mean value and standard deviation for a detection feature. The state-dependent sets of thresholds are then used at the appropriate time based upon a currently assessed state.

Figure 6A:
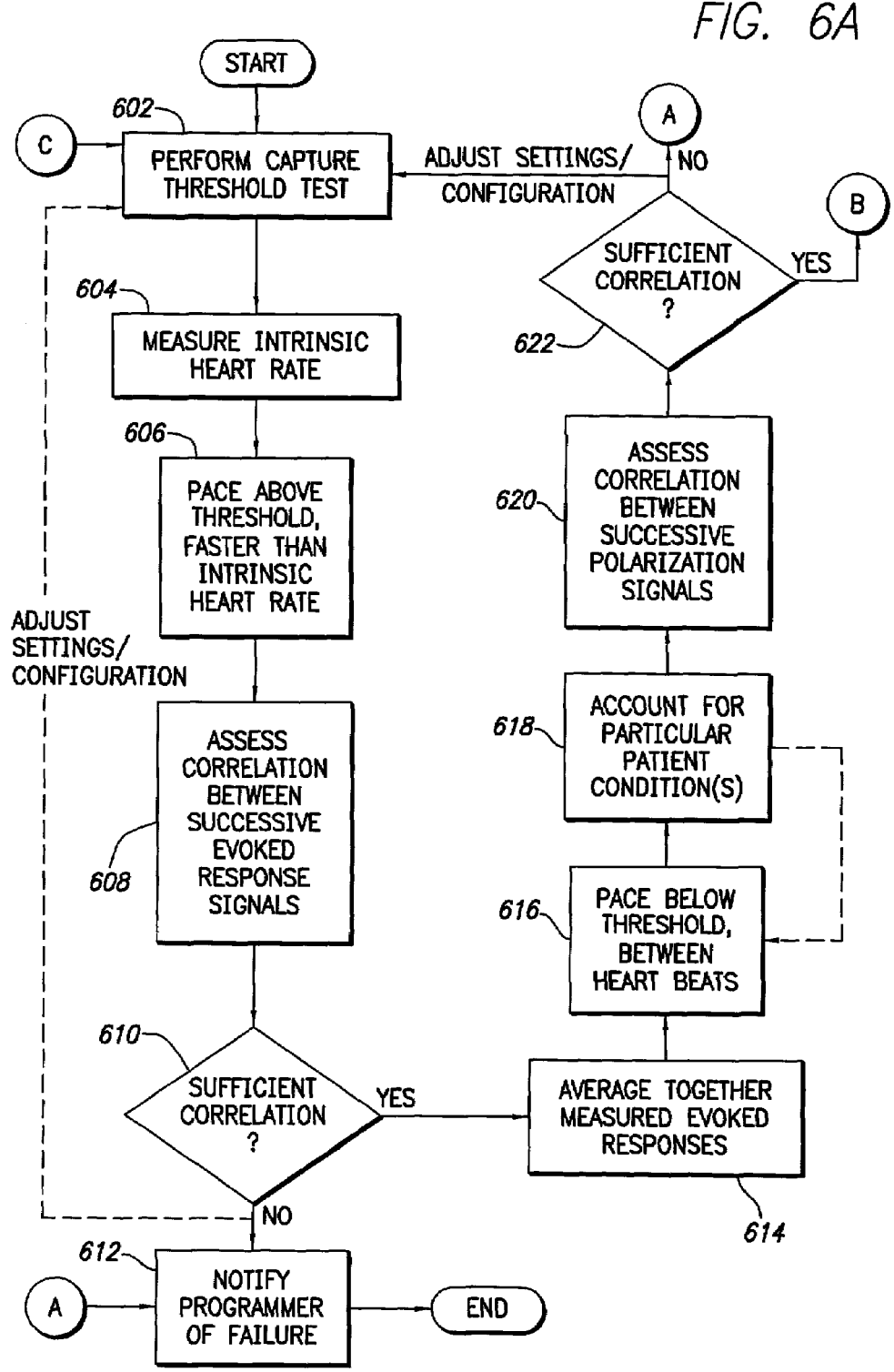
FIGS. 6A and 6B are a logic flow diagram of a calibrating control program executed by a microcontroller in an implantable stimulation device according to one embodiment of the invention.
Figure 6B:
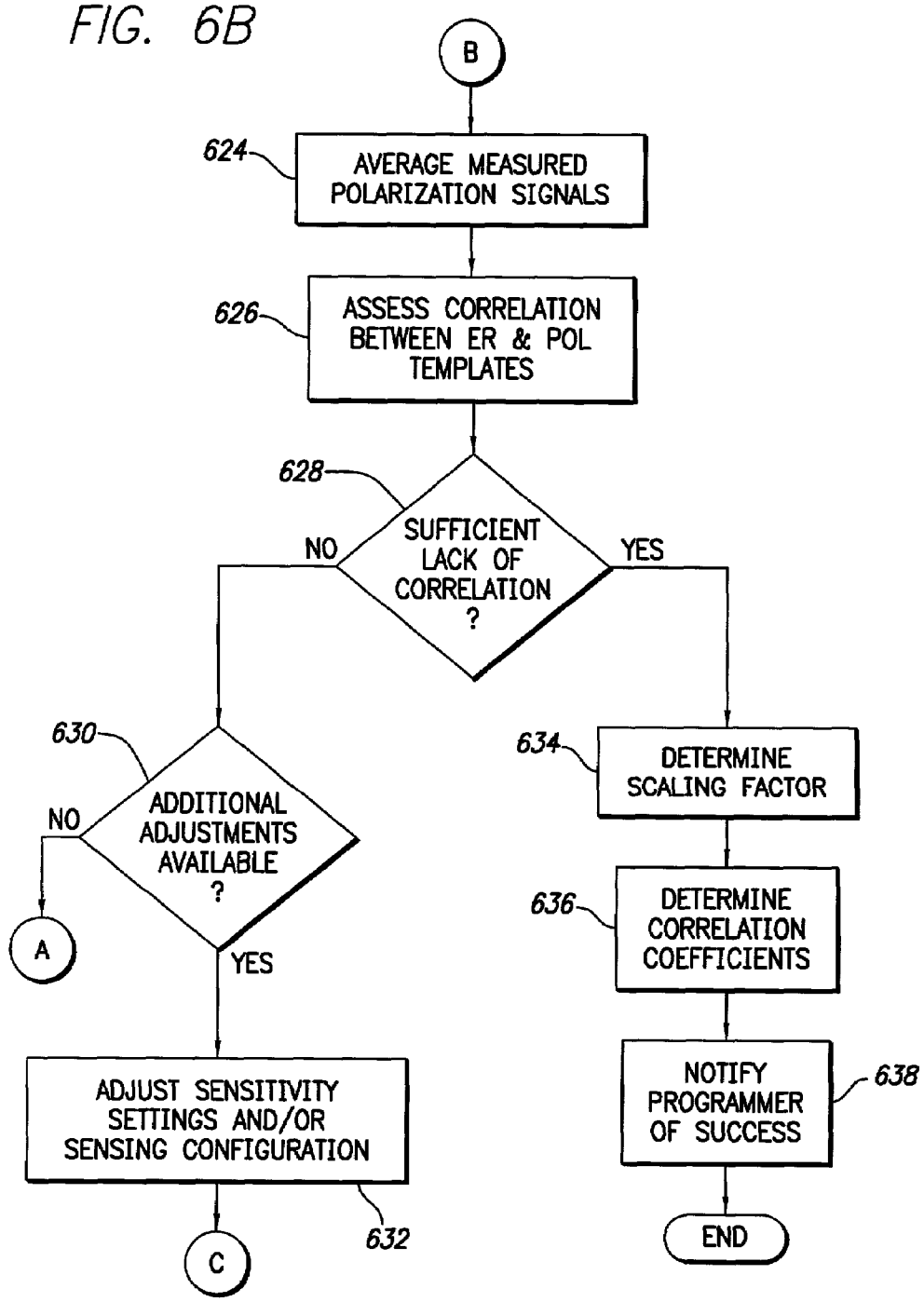

FIGS. 6A and 6B are a logic flow diagram of a calibrating control program executed by a microcontroller in an implantable stimulation device according to another embodiment of the invention. The logic flow diagram of FIGS. 6A and 6B represents an overview of the operation and novel features of one aspect of one embodiment of the stimulation device 10. Referring now to FIG. 6A, the calibrating process begins with step 602, in which a capture threshold test is performed. This capture threshold test identifies the patient's current capture threshold. Then in step 604, the patient's current intrinsic heart rate is measured. For patients who require regular pacing therapy, such as those with complete heart block, step 604 may be unnecessary.

Following the determination of capture threshold and intrinsic heart rate, the patient's heart is paced at a voltage level above the capture threshold, at a rate higher than the patient's intrinsic heart rate in step 606. This pacing step 606 ensures that the measured evoked responses are true evoked responses, which are not affected by fusion activity. During this pacing step 606, each sensed ER signal is stored.

In one embodiment, the voltage level is varied during step 606 to cover a number of output levels, each of which is above the capture threshold. This is done to ensure that the sensed ER signal has a consistent morphology across a range of output energy levels. Generally, however, this variation is not needed. Although the ER signal does change with posture, stress, and other variables that affect intracellular and extracellular ionic balance and tissue conduction velocity, it is consistent enough for reliability. The ER signal has a relatively unchanging, distinct morphology and relatively unchanging amplitude across different stimulation output energies, provided that actual capture of the heart is effected. This alternative embodiment may be used to add an additional safety measure.

In step 608, the correlation between the stored ER signals is assessed. In one embodiment, this correlation is performed by point by point subtraction and a correlation coefficient is assigned based on the magnitude of the mean square of the differences. In an alternative embodiment, this correlation is done using a standard true correlation technique (such as Pearson's or Spearman's coefficients) of the appropriate polynomial order. In one embodiment, the stored ER signals are compared using one or more of these correlation coefficients.

In step 610, the assessed correlation coefficients are checked to ensure that a sufficient correlation has been obtained. In one embodiment, each stored ER signal will be required to have a correlation measure greater than 0.8 when compared with each of the other stored ER signals. If sufficient correlation is found in step 610, control passes to step 614. If not, control passes to step 612.

In step 612, the programmer and/or attending physician are notified of the failure to find sufficient correlation among the stored ER signals. As shown, the process ends following step 612. In practice, however, the programmer may adjust the sensitivity settings and/or the sensing electrode configurations following step 612, then initiate the calibrating process again.

In addition, in one embodiment, the control program for the stimulating device automatically performs these adjustments. In this embodiment, steps 602 through 610 represent a loop in which multiple sensitivity settings and multiple sensing electrode configurations are tried by the stimulating device before a failure is reported in step 612. One such automatically adjusting calibration embodiment is designed to obtain the best configuration for sensing the evoked response. This configuration provides a consistent sensed ER signal that is maximally different from the POL signal.

Once sufficient correlation has been identified in step 610, control passes to step 614, in which the stored ER signals are averaged together. This averaged ER signal is the ER template, or capture template, used for future identification of evoked response.

Following step 614, the patient's heart is paced below the identified capture threshold in step 616. For example, in one embodiment, stimulation pulses equal to half the capture threshold are delivered to the patient's heart in between the normal heart beats. The signals sensed following the subthreshold pulses are the POL signals, and each such POL signal is stored for later analysis. Following step 616, the patient's particular condition is accounted for. This may be a single step after multiple pacing pulses, or it may be a step that is repeated with step 616 for each pacing pulse. For example, for patients with complete heart block, the patient's heart is paced with paired pulses. On the primary pulse, the patient's heart is paced at half the capture threshold voltage to acquire the data in step 616 and, after each such pulse, the patient's heart is stimulated with a second, suprathreshold pulse to ensure that the chamber contracts.

In one embodiment, the pulses delivered in step 616 are varied in terms of output energy. These variations are stored along with each POL signal. Because the POL signal varies in amplitude with the output energy of the stimulation pulse, the stored variations are useful in determining a scaling factor for a polarization template. However, studies have shown that features of the polarization artifact are highly linearly related to the pulse output energy. Thus, in one embodiment, the scaling factor is calculated directly using a present sensitivity setting and electrode configuration along with known properties of the electrodes being used.

Although the POL signal amplitude varies with stimulation pulse energy, the general POL signal morphology remains relatively unchanged. Thus, in an alternative embodiment, a standard true correlation coefficient is calculated and is used during normal operation, and no scaling factor is needed.

Following step 618, the correlation between the stored POL signals is assessed in step 620. In one embodiment, where the test pulses all have the same energy, this correlation is performed by point-by-point subtraction and a correlation coefficient is assigned by assessing the magnitude of the mean square of these differences. In an alternative embodiment, this correlation is done using a standard true correlation technique of the appropriate polynomial order. In one embodiment, the stored POL signals are compared in step 620 using one or more standard correlation coefficients.

In an embodiment where different test pulse energies are used, the assessment in step 620 either performs scaling before comparison or uses a standard true correlation technique as discussed above.

In step 622, the assessed correlation coefficients are checked to ensure that a sufficient correlation has been obtained. In one embodiment, each stored POL signal is required to have a correlation measure greater than 0.8 when compared with each of the other stored POL signals. If sufficient correlation is found in step 622, control passes to step 624 on FIG. 6B. If not, control passes to step 612.

In step 612, the programmer and/or attending physician are notified of the failure to find sufficient correlation among the stored POL signals. As shown, the process ends following step 612. In practice, however, the programmer may adjust the sensitivity settings and/or the sensing electrode configurations following step 612, then initiate the calibrating process again.

In addition, in one embodiment, the control program for the stimulating device automatically performs these adjustments. In this embodiment, steps 602 through 622 represent a loop in which multiple sensitivity settings and multiple sensing electrode configurations are tried by the stimulating device before a failure is reported in step 612. One such automatically adjusting calibration embodiment is designed to obtain the best configuration for sensing the polarization artifact. This configuration provides a consistent sensed POL signal that is maximally different from the ER signal.

Once sufficient correlation has been identified in step 622, control passes to step 624 on FIG. 6B, in which the stored POL signals are averaged together. This averaged POL signal is the POL template, or LOC template, used for future identification of the polarization artifact.

Following step 624, the ER template and the POL template are compared in step 626, by assessing the magnitude of a standard true correlation coefficient. This comparison is done to ensure that there is a sufficient lack of correlation between the two templates. In practice, the correlation between the two templates should be minimal, and any excessive correlation is reported to the programmer and/or the treating physician.

In step 628, the assessed correlation is compared with an expected lack of correlation. Generally, the assessed correlation should be less than 0.2. If there is a sufficient lack of correlation, control passes to step 634. If not, control passes to step 630. In step 630, an assessment is made, either by the control program itself or by the programmer after an appropriate prompt, whether additional adjustments to the sensitivity settings and/or the sensing electrode configurations are available. If not, control passes to step 612 on FIG. 6A, in which this failure is reported to the programmer. If additional adjustments are available, control passes to step 632, in which adjustments are made before the process returns to step 602 on FIG. 6A.

Once adequate ER and POL templates have been obtained, control passes to step 634, in which a scaling factor for the POL template is determined. As discussed previously, this scaling factor may not be necessary if the correlation technique used during normal operation does not require it. When the correlation technique does require a scaling factor, such as when a simple point-by-point subtraction method is employed, all the sampled data points in the present POL template are adjusted for each stimulation pulse using the following equation:

(1) $POL_{PRESENT}(n) = K \cdot (\text{Output Pulse Amplitude}) \cdot (\text{Output Pulse Width}) \cdot (POL_{TEST}(n))$  (1)

where K is the scaling factor determined in step 634, $POL_{TEST}(n)$ is the POL template generated during the calibration process, and $POL_{PRESENT}(n)$ is the POL template used for the sensed response to the present stimulation pulse.

Following step 634, the desired correlation coefficients for identifying capture and LOC are determined in step 636. In one embodiment, these correlation coefficients are fully programmable. Additionally, in one embodiment, these desired correlation coefficients are determined automatically in step 636 if no programmed values have been specified. Generally, the capture correlation coefficient and the LOC correlation coefficient are set to values between about 0.6 and about 0.8, for example about 0.7. Moreover, in one embodiment, the LOC correlation coefficient is set to a value less than the capture correlation coefficient, for example about 0.6, to introduce an additional safety margin.

When the desired correlation coefficients are determined in step 636, the values used are selected based upon the correlation assessed in step 626. A greater correlation between the ER template and the POL template translates into a greater value for the desired capture correlation coefficient and a lesser value for the desired LOC correlation coefficient. A lesser correlation between the ER template and the POL template translates into a lesser value for the desired capture correlation coefficient.

Moreover, in one embodiment, the desired correlation coefficients determined in step 636 are selected based upon additional criteria, including how closely the test ER signals correlated with each other and how closely the test POL signals correlated with each other. In addition, in one embodiment, the calibrating process also assesses fusion beats in the determination of the desired correlation coefficients in step 636.

Following step 636, the programmer and/or the attending physician is notified of the success of the calibration routine in step 638, before the process ends. In one embodiment, this calibration process is performed at implant, prior to discharge of the patient from the hospital, and during follow-up visits to ensure patient safety. Moreover, in an alternative embodiment, this calibration process is performed for multiple states, such as time of day, level of activity, etc., to obtain multiple capture templates and multiple LOC templates. The state-dependent templates are then used at the appropriate time based upon a currently assessed state.

Figure 7:
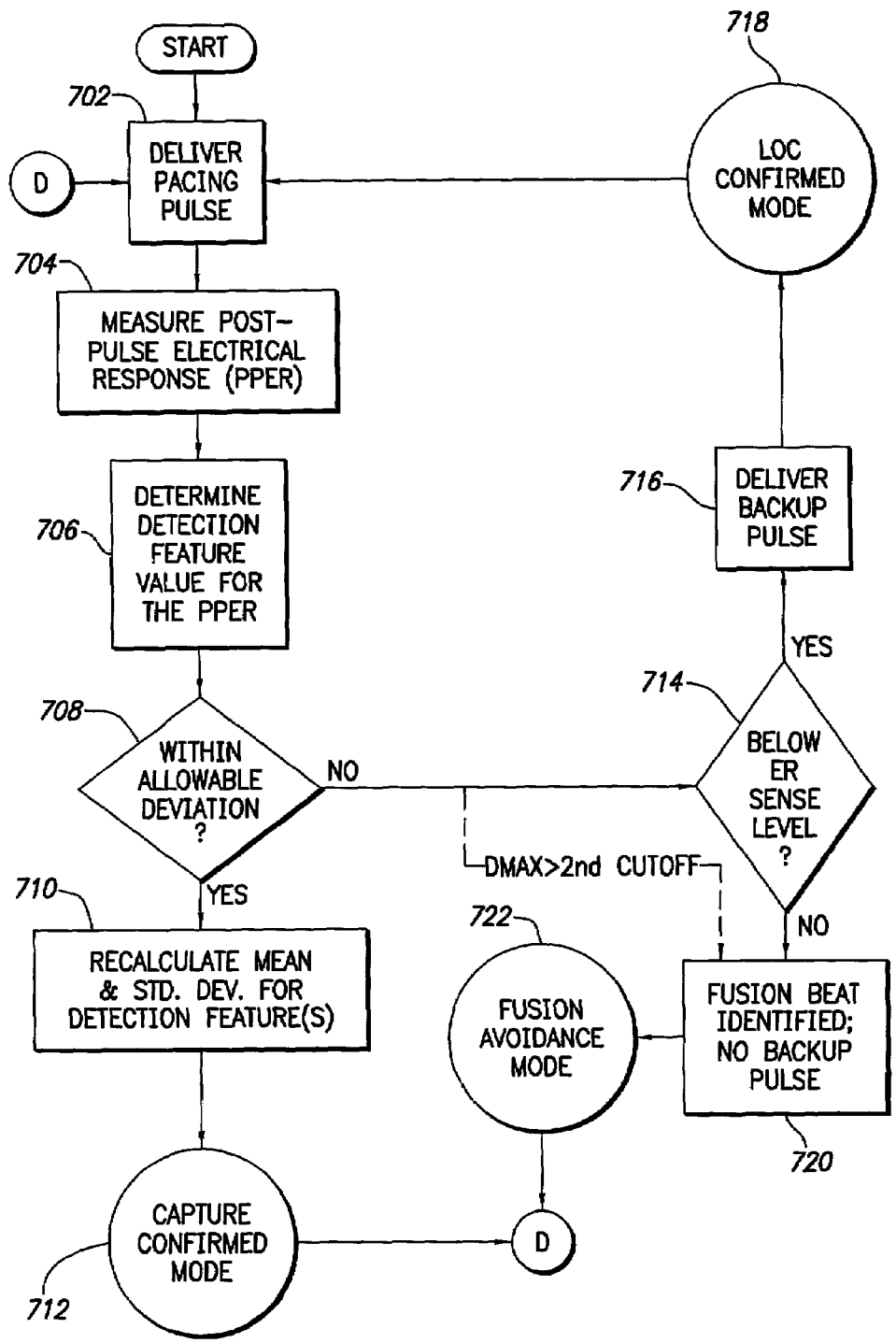
FIG. 7 is a logic flow diagram of an automatic fusion beat detecting control program executed by a microcontroller in an implantable stimulation device according to one embodiment of the invention.

FIG. 7 is a logic flow diagram of an automatic fusion beat detecting control program executed by a microcontroller in an implantable stimulation device according to one embodiment of the invention. The process begins with step 702 after the control program for the stimulation device has determined that a pacing pulse is necessary. In step 702, the necessary pacing pulse is delivered. Following this, the post-pulse electrical response (PPER) is measured in step 704. As is well understood in the art, the measuring step 704 is typically performed after a short time window, or blanking interval, to allow most of the polarization and amplifier artifact to be removed.

For example, when looking for the DMAX of the PPER, this short time window may be between about 5 and about 20 ms. The DMAX value for a PPER is typically found in a window from about 20 to about 120 ms following a ventricular pulse and a window from about 5 to about 60 ms following an atrial pulse. However, in an alternative embodiment of the invention, a very low polarizing lead electrode is used, such that the blanking interval may be set very short, for example the interval may be governed by the switching speed of the electrode configuration switch 74 in the stimulation device 10.

After step 704, a value for the detection feature or features of the PPER is determined in step 706. In one embodiment, multiple detection features are used, and a value for each is determined in step 706. Moreover, in one illustrative embodiment, the PDI is used as at least one of the detection features.

In step 708, the value for the detection feature is compared with an allowable deviation. As discussed previously, in one embodiment the allowable deviation is defined by the mean and the standard deviation for the detection feature and by a programmable number N, which defines the number of allowable standard deviations around the mean. If the detection feature value is within the allowable deviation, control passes to step 710. Otherwise, control passes to step 714.

The particular implementation of step 708 depends upon the selected detection feature or set of detection features. For example, in an embodiment where PDI is being used to identify ER, and both PDI and DMAX are being used to identify fusion beats, the DMAX value is checked first in step 708. If the DMAX value is above the second cutoff threshold, the PPER represents a fusion beat, and control passes immediately to step 720. If the DMAX is within its allowable deviation, the DMAX mean and standard deviation are recalculated. Then, the PDI is checked to determine whether it is within its allowable deviation. If so, control passes to step 710. If not, control passes to step 714.

In step 710, the mean and standard deviation for the detection feature are recalculated using the current detection feature value, thereby creating an automatically adjusting threshold for capture detection. In one embodiment, the mean and standard deviation for the detection feature are calculated using a set of value measurements with a fixed number of elements. This fixed number of elements may be limited to the last fifty ER detection feature values. In this fashion, the necessary processing time is reduced.

Following step 710, control passes to a capture confirmed mode 712, thus indicating that the heart was captured by the stimulation pulse and the PPER was an evoked response. It should be noted that because the morphology of fusion beats can vary widely, some fusion beats may be identified as an ER signal in steps 706 and 708. This occasional misidentification, however, does not harm the patient and does not detract from the overall benefits of the fusion beat discrimination performed by the present invention.

The capture confirmed mode 712 implements any process steps necessary to maintain the current pacing pulse energy, including turning off any fusion avoidance processes which would otherwise be in force. Generally, the capture confirmed mode 712 results in the stimulation device returning to its standard operations mode, wherein the heart is monitored to determine if a pacing pulse is needed, and wherein the heart is monitored for any other states detectable by the stimulation device, such as fibrillation, tachyarrhythmia, etc. Once the stimulation device determines that another pacing pulse is needed, the process returns to step 702.

If the detection feature value is not within the allowable deviation in step 708, control passes to step 714, in which the detection feature value is compared with the ER sense level. If the detection feature value is below the ER sense level, control passes to step 716, thus indicating that the heart was not captured by the stimulation pulse and the PPER was a polarization artifact. In step 716, a relatively large backup pulse is then delivered. Following this the process moves to a LOC confirmed mode 718. It should be noted that because the morphology of fusion beats can vary widely, some fusion beats may be identified as a POL signal in step 714. This occasional misidentification, however, does not harm the patient and does not detract from the overall benefits of the fusion beat discrimination performed by the present invention.

The LOC confirmed mode 718 implements any process steps necessary to regain capture. The particular LOC recovery processes executed by the control program will depend on the particular implementation of the stimulation device. The various approaches to dealing with a loss-of-capture condition are well known the art. Generally, once capture has been reacquired, the stimulation device returns to its standard operations mode, wherein the heart is monitored to determine if a pacing pulse is needed, and wherein the heart is monitored for any other states detectable by the stimulation device. Once the stimulation device determines that another pacing pulse is needed, the process returns to step 702.

If the detection feature value is not below the ER sense level in step 714, control passes to step 720. Step 720 is not a traditional process step in that, in some embodiments, no operation is performed in step 720. This step is included, however, for the purpose of clarity.

If the process reaches step 720, this means that the PPER is a fusion beat, and thus no backup pulse is necessary. In this embodiment, in order to be classified as a fusion beat, the detection feature of the PPER is above the ER sense level value, and also deviates from the mean value by some preset number of deviations. In one embodiment, step 720 is used to perform any necessary storage of the PPER as historical data.

In addition, in one embodiment, the process enters a fusion avoidance mode 722 after a fusion beat has been identified. Various fusion avoidance techniques, such as positive/negative rate or AV/PV hysteresis, are well known in the art and thus are not discussed in detail herein. Once the particular fusion avoidance mode is set, the process returns to normal operations, subject to the particular fusion avoidance technique. The heart is monitored to determine if a pacing pulse is needed, and the heart is monitored for any other states that are detectable by the stimulation device. Once the stimulation device determines that another pacing pulse is needed, the process returns to step 702.

Figure 8:
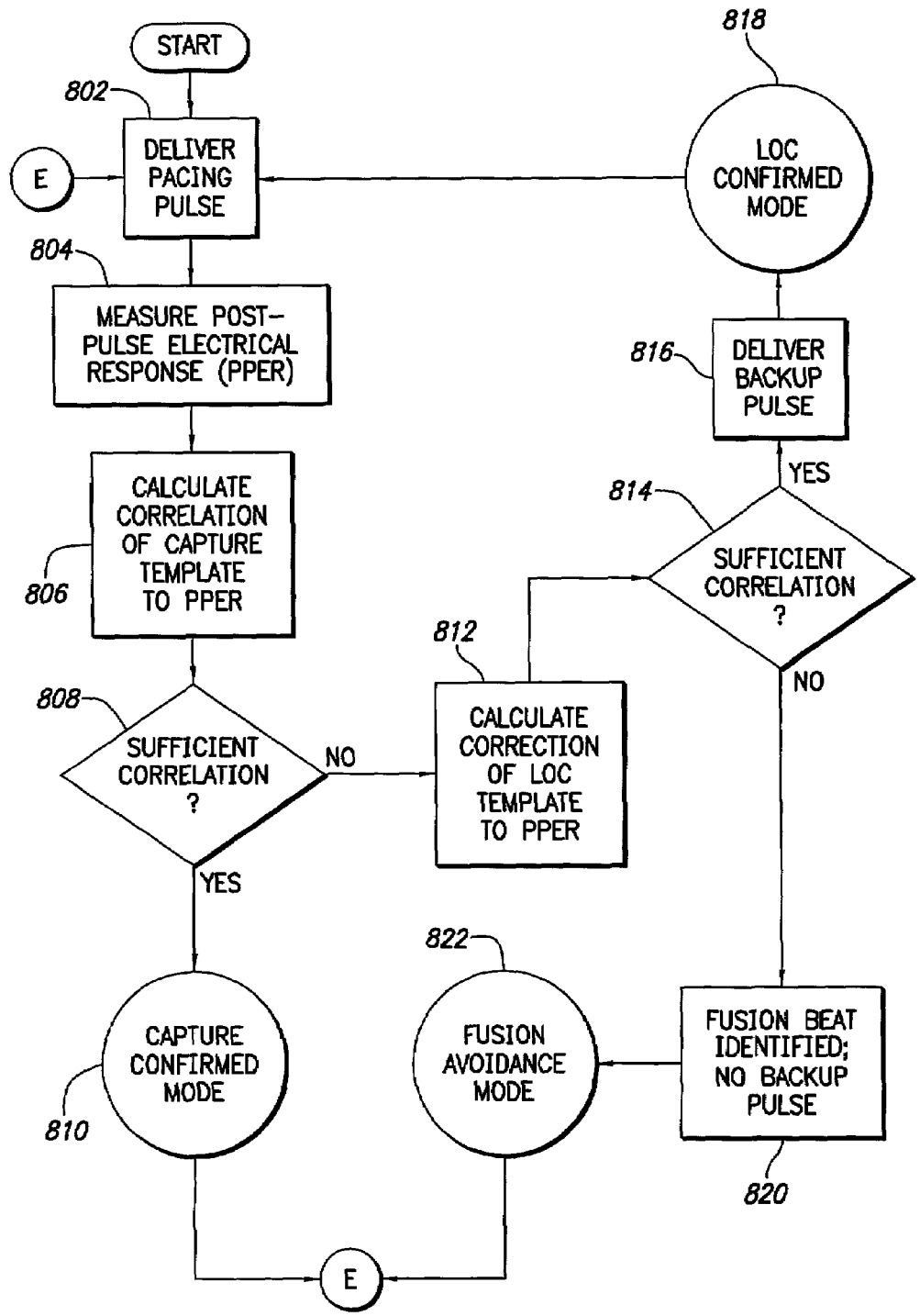
FIG. 8 is a logic flow diagram of an automatic fusion beat detecting control program executed by a microcontroller in an implantable stimulation device according to another embodiment of the invention.

FIG. 8 is a logic flow diagram of an automatic fusion beat detecting control process executed by a microcontroller in an implantable stimulation device according to one embodiment. The process begins with step 802 after the control program for the stimulation device has determined that a pacing pulse is necessary. In step 802, the necessary pacing pulse is delivered. Following this, the post-pulse electrical response (PPER) is measured in step 804. As is well understood in the art, and as described in detail above, the measuring step 804 should usually be performed after a short time window, or blanking interval, to allow most of the polarization and amplifier artifact to be removed.

After step 804, a correlation coefficient is calculated based on a comparison of the PPER and the capture template. In one embodiment, this correlation coefficient is calculated in step 806 using a template matching algorithm. This template matching may be implemented using a simple direct comparison, such as subtraction of the amplitudes, or it may be implemented using a true correlation technique, such as R-squared correlation, or any other suitable technique.

In addition, in one embodiment, a detection feature, such as PDI or DMAX, is calculated, or a combination of such detection features are calculated from the present PPER instead of by comparing a correlation coefficient to a capture template. Moreover, in one embodiment, the use of a detection feature includes the use of the automatically adjusting detection threshold discussed previously in connection with FIG. 7.

Use of such detection features in place of traditional template matching techniques can significantly reduce processing time without significantly decreasing the reliability of the comparison, provided that the detection feature(s) is sufficiently robust to accurately identify capture and LOC. For a more detailed description of various template matching techniques, see U.S. Pat. No. 5,400,795, entitled "Method of Classifying Heart Rhythms by Analyzing several Morphology Defining Metrics Derived for a Patient's QRS Complex" (Murphy et al.), and U.S. Pat. No. 5,417,718, entitled "System for Maintaining Capture in an Implantable Pulse Generator" (Kleks et al.). Both U.S. Pat. Nos. 5,400,795 and U.S. Pat. No. 5,417,718 are hereby incorporated herein by reference.

In step 808, the calculated correlation coefficient is compared with the desired capture correlation coefficient to identify whether the PPER represents an evoked response. If the calculated correlation coefficient is sufficiently large, control passes to a capture confirmed mode 810, thus indicating that the heart was captured by the stimulation pulse and the PPER was an evoked response. It should be noted that because the morphology of fusion beats can vary widely, some fusion beats may be identified as an ER signal in steps 806 and 808. This occasional misidentification, however, does not harm the patient and does not detract from the overall benefits of the fusion beat discrimination performed by the present invention.

The capture confirmed mode 810 implements any process steps necessary to maintain the current pacing pulse energy, including turning off any fusion avoidance processes which would otherwise be in force. Generally, the capture confirmed mode 810 indicates that the stimulation device returns to its standard operations mode, wherein the heart is monitored to determine if a pacing pulse is needed, and wherein the heart is monitored for any other states that are detectable by the stimulation device, such as fibrillation, tachyarrhythmia, etc. Once the stimulation device determines that another pacing pulse is needed, the process returns to step 802.

If the calculated correlation coefficient is not sufficiently large in step 808, control passes to step 812, in which a correlation coefficient is calculated for a comparison between the PPER and the LOC template. In one embodiment, this correlation coefficient is calculated in step 812 using a template matching algorithm. This template matching may be implemented using a simple direct comparison of the scaled POL template with the PPER, such as subtraction of the amplitudes, or it may be implemented using a true correlation technique, such as R-squared correlation.

In addition, in one embodiment, instead of a correlation coefficient to a capture template, a detection feature such as PDI or DMAX, or a combination of such detection features, is calculated from the PPER. Moreover, in one embodiment, the use of a detection feature includes the use of the automatically adjusting detection threshold discussed previously in connection with FIG. 7.

Use of such detection features in place of traditional template matching techniques can significantly reduce processing time without significantly decreasing the reliability of the comparison, provided that the detection feature(s) is sufficiently robust to accurately identify capture and LOC.

In one embodiment, capture is assessed by comparing a detection feature to an ER sense level to save processing time, and the LOC correlation coefficient is calculated using template matching/correlation, thereby avoiding the need to scale the polarization signal template. For a more detailed description of various template matching techniques, see U.S. Pat. Nos. 5,400,795 and 5,417,718, discussed previously.

In step 814, the calculated correlation coefficient is compared with the desired LOC correlation coefficient to identify whether the PPER represents a polarization artifact. If the calculated correlation coefficient is sufficiently large, control passes to step 816, thus indicating that the heart was not captured by the stimulation pulse and the PPER was a polarization artifact. In step 816, a backup pulse of sufficient energy to ensure capture is delivered. Following this the process moves to a LOC confirmed mode 818. It should be noted that because the morphology of fusion beats can vary widely, some fusion beats may be identified as a POL signal in steps 812 and 814. This occasional misidentification, however, does not harm the patient and does not detract from the overall benefits of the fusion beat discrimination performed by the present invention The LOC confirmed mode 818 implements any process steps necessary to regain capture. The particular LOC recovery processes executed by the control program will depend on the particular implementation of the stimulation device. The various alternative approaches to dealing with a lossof-capture condition are well known the art. Generally, once capture has been reacquired, the stimulation device returns to its standard operations mode, wherein the heart is monitored to determine if a pacing pulse is needed, and wherein the heart is monitored for any other states that are detectable by the stimulation device. Once the stimulation device determines that another pacing pulse is needed, the process returns to step 802.

If the calculated correlation coefficient is not sufficiently large in step 814, control passes to step 820. Step 820 is not a traditional process step in that, in some embodiments, no operation is performed in step 820. This step is included, however, for the purpose of clarity.

Once the process reaches step 820, this means that the PPER is neither an evoked response indicating capture nor a polarization artifact indicating LOC. Since the PPER is neither ER nor POL, it is classified as a fusion beat, and thus no backup pulse is issued. In one embodiment, step 820 is used to perform any necessary storage of the PPER as historical data.

In addition, in one embodiment, the process enters a fusion avoidance mode 822 after a fusion beat has been identified. The various available fusion avoidance techniques, such as positive/negative rate or AV/PV hysteresis, are well known in the art and thus are not discussed in detail herein. Once the particular fusion avoidance mode is set, the process returns to normal operations, subject to the particular fusion avoidance technique. The heart is monitored to determine if a pacing pulse is needed, and the heart is monitored for any other states detectable by the stimulation device. Once the stimulation device determines that another pacing pulse is needed, the process returns to step 802.

While various embodiments of the present invention have been described above, it should be understood that they have been presented by way of example only, and are not meant to limit the scope of the invention. It is to be understood that the description and drawings represent the presently preferred embodiment(s) of the invention and are, as such, representative of the subject matter which is broadly contemplated by the present invention.

Furthermore, the scope of the present invention fully encompasses other embodiments that may become obvious to those skilled in the relevant art(s). Thus, the breadth and scope of the present invention should not be limited by any of the above-described exemplary embodiments, but should be defined only in accordance with the issued claims and their equivalents.

What is claimed is:

1. A method for identifying a fusion beat following delivery of a stimulating pulse in myocardial tissue, comprising:
    (a) sensing a post-pulse electrical response;
    (b) assessing a detection feature of the post-pulse electrical response with at least one capture detection function to determine whether the post-pulse electrical response corresponds with capture;
    (c) assessing the detection feature of the post-pulse electrical response with at least one loss-of-capture detection function to determine whether the post-pulse electrical response corresponds with loss-of-capture; and
    (d) classifying the post-pulse electrical response as a fusion beat if the post-pulse electrical response does not correspond with either capture or loss-of-capture.

2. The method of claim 1, further comprising computing a value for the detection feature for the post-pulse electrical response.

3. The method of claim 2, wherein the detection feature comprises a paced depolarization integral for the post-pulse electrical response.

4. The method of claim 2, wherein the detection feature comprises a peak negative amplitude for the post-pulse electrical response.

5. The method of claim 2, wherein the detection feature comprises one of a positive and negative peak slope for the post-pulse electrical response.

6. The method of claim 2, wherein:
    (a) assessing the detection feature of the post-pulse electrical response with the capture detection function comprises:
        (i) comparing the computed value with a first evoked response sense level threshold; and
        (ii) updating the first evoked response sense level threshold, if a state of capture is identified by the capture comparison; and
    (b) assessing the detection feature of the post-pulse electrical response with the loss-of-capture detection function comprises comparing the computed value with a second evoked response sense level threshold.

7. The method of claim 6, wherein the updating of the first evoked response sense level threshold comprises recalculating a mean value and a measure of variance around the mean value for the detection feature using the computed value for the detection feature, if the computed value falls within a predetermined measure of variance around the mean value.

8. The method of claim 7, wherein the detection feature comprises a maximum positive slope for the post-pulse electrical response, and wherein comparing the computed value with the first evoked response sense level threshold comprises checking whether the computed value falls within a predetermined measure of variance around the mean value.

9. The method of claim 8, wherein the predetermined measure of variance is programmable.

10. The method of claim 1, wherein assessing the post-pulse electrical response with the capture detection function comprises comparing the post-pulse electrical response with an evoked response signal recognition template, and wherein assessing the post-pulse electrical response with the loss-of-capture detection function comprises comparing the post-pulse electrical response with a polarization signal recognition template.

11. The method of claim 10, wherein the polarization signal recognition template comparison comprises performing a selected correlation between the post-pulse electrical response and the polarization signal recognition template to obtain a loss-of-capture correlation coefficient, and the evoked response signal recognition template comparison comprises performing a selected correlation between the post-pulse electrical response and the evoked response signal recognition template to obtain a capture correlation coefficient.

12. The method of claim 11 wherein the selected correlation comprises:
    aligning the post-pulse electrical response with the signal recognition template;
    calculating a Pearson's correlation coefficient between corresponding data points in the post-pulse electrical response and the signal recognition template; and
    defining the Pearson's correlation coefficient as a measure of correlation between the post-pulse electrical response and the signal recognition template.

13. The method of claim 10, wherein:
    (a) the polarization signal recognition template comparison comprises performing a selected correlation between the post-pulse electrical response and the polarization signal recognition template to obtain a LOC correlation coefficient; and (b) the evoked response signal recognition template comparison comprises:
  (i) aligning the post-pulse electrical response with the evoked response signal recognition template;
  (ii) subtracting the post-pulse electrical response from the evoked response signal recognition template; and
  (iii) checking the resulting difference for excessive magnitude, where the resulting difference is one of the sum of the differences and the mean of the square of the differences.

14. A method for detecting a fusion beat following delivery of a stimulating pulse in myocardial tissue, comprising:
(a) sensing a post-pulse electrical response;
(b) computing a value for a detection feature for the post-pulse electrical response;
(c) classifying the post-pulse electrical response as a fusion beat if the value falls outside a prescribed deviation and not within a loss-of-capture range specified by an evoked response sense level threshold, wherein the prescribed deviation is determined using a moving average and measure of variance for the detection feature; and
(d) recalculating the moving average and the measure of variance using the value of the detection feature for the post-pulse electrical response if the value falls within the prescribed deviation.

15. The method of claim 14, further comprising:
(a) selecting the detection feature;
(b) determining the evoked response sense level threshold for the detection feature; and
(c) generating the moving average and the measure of variance for determined values for the detection feature for a set of post-pulse electrical responses identified as evoked response signals.

16. The method of claim 15, wherein the determining step comprises setting the evoked response sense level threshold to a predetermined value between a mean value for the determined values and a maximum observed value for the detection feature for a set of post-pulse electrical responses identified as polarization signals.

17. The method of claim 16, further comprising programming the evoked response sense level threshold.

18. The method of claim 17, wherein programming the evoked response sense level threshold comprises setting the evoked response sense level threshold to a value between a mean value for the determined values and a maximum observed value for the detection feature for a set of post-pulse electrical responses identified as polarization signals.

19. The method of claim 14, wherein the detection feature comprises a maximum positive slope for the post-pulse electrical response.

20. The method of claim 19, wherein the prescribed deviation comprises a first deviation and a second deviation, and wherein the classifying step comprises:
(a) first-classifying the post-pulse electrical response as a fusion beat if the value falls above the first deviation;
(b) terminating the classification step if the post-pulse electrical response is classified as a fusion beat in the first-classifying step, thereby reducing an amount of time needed to carry out the method; and
(c) second-classifying the post-pulse electrical response as a fusion beat if the value falls below the second deviation and above the evoked response sense level threshold.

21. The method of claim 20, wherein the first deviation and the second deviation are separately programmable.

22. The method of claim 20, wherein the detection feature is only used to detect fusion beats and not evoked responses.

23. The method of claim 14, wherein the prescribed deviation is programmable.

24. The method of claim 14, wherein the detection feature comprises a peak negative amplitude for the post-pulse electrical response.

25. The method of claim 14, wherein the detection feature comprises a paced depolarization integral for the post-pulse electrical response.

26. The method of claim 25, wherein the prescribed deviation is three standard deviations and the loss-of-capture range comprises a low-end equal to zero and a high-end equal to the evoked response sense level threshold.

27. A system for detecting fusion beats comprising:
post-pulse electrical response sensing circuitry; and
a control unit coupled with the sensing circuitry, the control unit being configured to:
assess a detection feature of a post-pulse electrical response with at least one capture detection function to determine whether the post-pulse electrical response corresponds with capture;
assess the detection feature of the post-pulse electrical response with at least one loss-of-capture detection function to determine whether the post-pulse electrical response corresponds with loss-of-capture; and
classify the post-pulse electrical response as a fusion beat if the post-pulse electrical response does not correspond with either capture or loss-of-capture.

28. The stimulation device of claim 27, wherein the control unit comprises a microcontroller and a control program.

29. The stimulation device of claim 27, wherein the control unit is further configured to enter a fusion avoidance mode if the post-pulse electrical response is classified as a fusion beat.

30. The stimulation device of claim 27, wherein the control unit is further configured to compute a value for the detection feature for the post-pulse electrical response.

31. The stimulation device of claim 30, wherein:
the capture detection function compares the computed value for the detection feature with a first evoked response sense level threshold and updates the first evoked response sense level threshold; and
the loss-of-capture detection function compares the computed value for the detection feature with a second evoked response sense level threshold.

32. The stimulation device of claim 31, wherein the update performed by the capture detection function comprises recalculating a mean value and a measure of variance around the mean value for the detection feature using the current computed value for the detection feature, if the current computed value falls within a predetermined measure of variance around the mean value.

33. The stimulation device of claim 30, wherein the detection feature comprises a paced depolarization integral for the post-pulse electrical response.

34. The stimulation device of claim 30, wherein the detection feature comprises a peak negative amplitude for the post-pulse electrical response.

35. The stimulation device of claim 30, wherein the detection feature comprises a maximum positive slope for the post-pulse electrical response.

36. The stimulation device of claim 27, wherein;
the capture detection function compares the post-pulse electrical response with an evoked response signal recognition template; and
the loss-of-capture detection function compares the post-pulse electrical response with a polarization signal recognition template.

37. The stimulation device of claim 36, wherein:
the evoked response signal recognition template comparison comprises performing a selected correlation between the post-pulse electrical response and the evoked response signal recognition template to obtain a capture correlation coefficient; and
the polarization signal recognition template comparison comprises performing a selected correlation between the post-pulse electrical response and the polarization signal recognition template to obtain a LOC correlation coefficient.

38. A stimulation device comprising:
a pulse generator;
post-pulse electrical response sensing circuitry; and
a control unit coupled with the pulse generator and the sensing circuitry, the control unit being configured to:
compute a value for a detection feature for a post-pulse electrical response;
classify the post-pulse electrical response as a fusion beat if the value falls outside a prescribed deviation and not within a loss-of-capture range specified by an evoked response sense level threshold, wherein the prescribed deviation is determined using a moving average and a measure of variance around the moving average for the detection feature; and
recalculate the moving average and the measure of variance using the value of the detection feature for the post-pulse electrical response if the value falls within the prescribed deviation.

39. The stimulation device of claim 38, wherein the control unit comprises a microcontroller and a control program.

40. The stimulation device of claim 38, wherein the control unit is further configured to enter a fusion avoidance mode if the post-pulse electrical response is classified as a fusion beat.

41. The stimulation device of claim 38, wherein the detection feature comprises a maximum positive slope for the post-pulse electrical response.

42. The stimulation device of claim 41, wherein the detection feature is only used to detect fusion beats and not evoked responses.

43. The stimulation device of claim 41, wherein the prescribed deviation comprises a first deviation and a second deviation, and wherein the control unit is further configured to:
classify the post-pulse electrical response as a fusion beat, without further checking of the value, if the value falls above the first deviation; and
classify the post-pulse electrical response as a fusion beat if the value falls below the second deviation and above the evoked response sense level threshold.

44. The stimulation device of claim 43, wherein the first deviation and the second deviation are separately programmable.

45. The stimulation device of claim 38, wherein the detection feature comprises a peak negative amplitude for the post-pulse electrical response.

46. The stimulation device of claim 38, wherein the detection feature comprises a paced depolarization integral for the post-pulse electrical response.

47. The stimulation device of claim 46, wherein the prescribed deviation is three standard deviations and the loss-of-capture range comprises a low-end equal to zero and a high-end equal to the evoked response sense level threshold.

48. The stimulation device of claim 46, wherein the prescribed deviation is programmable.

49. A stimulation device comprising:
sensing means for sensing a post-pulse electrical response; and
control means coupled with the sensing means, the control means comprising means for comparing a value of a detection feature of the post-pulse electrical response to a first threshold to identify capture, means for comparing the value of the detection feature of the post-pulse electrical response to a second threshold to identity loss-of-capture and means for identifying a fusion beat, wherein the fusion beat identification is the default identification resulting from a failure to confirm capture or loss-of-capture.

50. A stimulation device comprising:
sensing means for sensing a post-pulse electrical response; and
control means coupled with the sensing means, the control means comprising:
means for computing a value for a detection feature for a post-pulse electrical response;
means for classifying the post-pulse electrical response as a fusion beat if the value falls outside a prescribed deviation and not within a loss-of-capture range specified by an evoked response sense level threshold, wherein the prescribed deviation is determined using a moving average and a measure of variance around the moving average for the detection feature; and
means for recalculating the moving average and the measure of variance using the value of the detection feature for the post-pulse electrical response if the value falls within the prescribed deviation.

* * * * *